US009275844B2

(12) United States Patent  
Bogan et al.

(10) Patent No.: US 9,275,844 B2  
(45) Date of Patent: Mar. 1, 2016

(54) APPARATUS AND METHOD FOR NANOFLOW LIQUID JET AND SERIAL FEMTOSECOND X-RAY PROTEIN CRYSTALLOGRAPHY

(71) Applicants: Michael J. Bogan, San Francisco, CA (US); Hartawan Laksmono, Sunnyvale, CA (US); Raymond G. Sierra, Stanford, CA (US)

(72) Inventors: Michael J. Bogan, San Francisco, CA (US); Hartawan Laksmono, Sunnyvale, CA (US); Raymond G. Sierra, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 209 days.

(21) Appl. No.: 13/896,303

(22) Filed: May 16, 2013

(65) Prior Publication Data

US 2013/0308756 A1 Nov. 21, 2013

Related U.S. Application Data

(60) Provisional application No. 61/647,676, filed on May 16, 2012.

(51) Int. Cl.
*H01J 49/16* (2006.01)
*H01J 49/04* (2006.01)
(Continued)

(52) U.S. Cl.
CPC .............. *H01J 49/167* (2013.01); *H01J 49/04* (2013.01); *H01J 49/0404* (2013.01);
(Continued)

(58) Field of Classification Search
CPC .............. C12Q 2565/60; C12Q 2565/626; C12Q 2565/627; C12Q 2565/629; C12M 1/34; C12M 1/343; C12M 1/3446; C12M 29/00; C12M 29/06; C12M 29/10; C12M 29/14; C12M 29/16; C12M 33/04; C12M 33/07; C12M 41/00; G01T 1/00; G01T 1/36; G01N 5/10; G01N 5/1043; G01N 15/14; G01N 23/20; G01N 23/20008; G01N 23/20025; H01J 49/00; H01J 49/0004; H01J 49/0013; H01J 49/0027; H01J 49/0095; H01J 49/02; H01J 49/04; H01J 49/0404; H01J 49/0431; H01J 49/0445; H01J 49/165; H01J 49/167; H01J 49/26

USPC .............. 378/70, 71, 73, 79, 80, 86, 87, 204, 378/208, 210; 436/173, 174, 180, 52, 148, 436/205

See application file for complete search history.

(56) References Cited

U.S. PATENT DOCUMENTS 6,252,225 B1 * 6/2001 Takada et al. ................. 250/288
6,297,499 B1 * 10/2001 Fenn ............................. 250/288

(Continued)

OTHER PUBLICATIONS

Gallmaier et al, "Nano ES GEMMA and PDMA, New Tools for the Analysis of Nanobioparticles—Protein Complexes, Lipoparticles and Viruses", "Journal of the American Society for Mass Spectrometry", 2008, pp. 1062-1068, vol. 19, No. 8, Publisher: The American Society for Mass Spectrometry, Published in: http://link.springer.com/content/pdf/10.1016%2Fj.jasms.2008.05.017.pdf.

(Continued)

*Primary Examiner* — Anastasia Midkiff
(74) *Attorney, Agent, or Firm* — Beusse Wolter Sanks & Maire, PLLC; Eugene J. Molinelli

(57) ABSTRACT

Techniques for nanoflow serial femtosecond x-ray protein crystallography include providing a sample fluid by mixing a plurality of a first target of interest with a carrier fluid and injecting the sample fluid into a vacuum chamber at a rate less than about 4 microliters per minute. In some embodiments, the carrier fluid has a viscosity greater than about 3 centipoise.

19 Claims, 17 Drawing Sheets

(51) Int. Cl.
*B01J 4/00* (2006.01)
*G01N 23/20* (2006.01)

(52) U.S. Cl.
CPC ........ *H01J 49/0431* (2013.01); *H01J 49/0445* (2013.01); *H01J 49/165* (2013.01); *B01J 4/002* (2013.01); *G01N 23/20* (2013.01); *G01N 23/20025* (2013.01)

(56) References Cited

U.S. PATENT DOCUMENTS

| | | | | |
|---|---|---|---|---|
| 7,315,020 | B2* | 1/2008 | Park et al. | 250/288 |
| 7,544,932 | B2* | 6/2009 | Janini et al. | 250/288 |
| 8,227,750 | B1* | 7/2012 | Zhu et al. | 250/288 |
| 2012/0025071 | A1* | 2/2012 | Mordehai et al. | 250/287 |
| 2013/0214154 | A1* | 8/2013 | McEwen et al. | 250/288 |
| 2014/0166875 | A1* | 6/2014 | Trimpin | 250/282 |

OTHER PUBLICATIONS

R. Alonsomori et al., "Energy-dispersive X-ray emission spectroscopy using an X-ray free-electron laser in a shot-by-shot mode", "Proceedings of the National Academy of Science", 2012, pp. 19103-19107, vol. 109, No. 47, Publisher: National Academy of Science, Published in: http://www.pnas.org/content/early/2012/10/31/1211384109.full.pdf.

A. Aquila et al., "Time-resolved protein nanocrystallography using an X-ray free-electron laser", "Optics Express", 2012, pp. 2706-2716, vol. 20, No. 3, Publisher: Optical Society of America, Published in: http://www.opticsinfobase.org/view_article.cfm?gotourl=http%3A%2F%2Fwww%2Eopticsinfobase%2Eorg%2FDirectPDFAccess%2FC1F39BDB-ABF7-CA5C-58464F1C417CC7EC.

A. Barty et al., "Self-terminating diffraction gates femtosecond X-ray nanocrystallography measurements", "Nature Photonics", 2011, pp. 35-40, vol. 6, Publisher: Nature Publishing Group, Published in: http://www.nature.com.proxy.library.cornell.edu/nphoton/journal/v6/n1/full/nphoton.2011.297.html.

W. Benner et al., "Non-destructive characterization and alignment of aerodynamically focused particles beams using single particle charge", "Journal of Aerosal Science", 2008, pp. 917-928, vol. 39, Publisher: Elsevier, Published in: http://ac.els-cdn.com/S0021850208001043/1-s2.0-S0021850208001043-main.pdf?_tid=2ebae984-f4ca-11e2-a924-00000aacb361&acdnat=1374716178_d1c193748074e03c.

M. Bogan et al., "Single Particle X-ray Diffractive Imaging", "Nano Letters", 2008, pp. 310-316, vol. 8, No. 1, Publisher: American Chemical Society, Published in: http://pubs.acs.org/doi/abs/10.1021/nl072728k.

H. Chapman et al., "Femtosecond X-ray protein nanocrystallography", "Nature", 2011, pp. 73-77, vol. 470, Publisher: Nature Publishing Group, Published in: http://www.nature.com/nature/journal/v470/n7332/full/nature09750.html.

D. Deponte et al., "Gas dynamic virtual nozzle for generation of microscopic droplet streams", "Journal of Physics D: Applied Physics", 2008, pp. 1-7, vol. 41, No. 19, Publisher: Institute of Physics Publishing, Published in: http://iopscience.iop.org/0022-3727/41/19/195505.

D. Deponte et al., "SEM Imaging of Liquid Jets", "Micron", 2009, pp. 507-509, vol. 40, No. 4, Publisher: Elsevier, Published in: http://www.sciencedirect.com/science/article/pii/S0968432808002643.

D. Deponte et al., "Sample Injection for Pulsed X-ray Sources", "Proceedings of SPIE", 2011, vol. 8078, Publisher: Society of Photo-Optical Instrumentation Engineers, Published in: http://proceedings.spiedigitallibrary.org/proceeding.aspx?articleid=1271808.

M. Hunter et al., "X-ray Diffraction from Membrane Protein Nanocrystals", "Biophysical Journal", 2011, pp. 198-206, vol. 100, No. 1, Publisher: Cell Press, Published in: http://www.ncbi.nlm.nih.gov/pmc/articles/PMC3010013/pdf/main.pdf.

L. Johansson et al., "Lipidic phase membrane protein serial femtosecond crystallography", "Nature Methods", 2012, pp. 263-266, vol. 9, No. 3, Publisher: Nature Publishing Group, Published in: http://www.nature.com/nmeth/journal/v9/n3/full/nmeth.1867.html#access.

J. Jung et al., "Generation of Nonagglomerated Airborne Bacteriophage Particles Using an Electrospray Technique", "Analytical Chemistry", 2009, pp. 2985-2990, vol. 81, No. 8, Publisher: American Chemical Society, Published in: http://pubs.acs.org/doi/abs/10.1021/ac802584z.

J. Kern et al., "Room temperature femtosecond X-ray diffraction of photosystem II microcrystals", "Proceedings of the National Academy of Sceinces", 2012, pp. 9721-9726, vol. 109, No. 25, Publisher: National Academy of Sciences, Published in: http://www.pnas.org/content/early/2012/05/31/1204598109.abstract.

J. Kern et al., "Simultaneous Femtosecond X-ray Spectroscopy and Diffraction of Photosystem II at Room Temperature", "Science", 2013, pp. 491-495, vol. 340, Publisher: American Association for the Advancement of Science, Published in: http://www.sciencemag.org/content/340/6131/491.abstract.

R. Koopmann et al., "In vivo protein crystallization opens new routes in structural biology", "Nature Methods", 2012, pp. 259-264, vol. 9, No. 3, Publisher: Nature Publishing Group, Published in: http://www.nature.com/nmeth/journal/v9/n3/full/nmeth.1859.html.

B. Ku et al., "Electrohydrodynamic spraying characteristics of glycerol solutions in vacuum", "Journal of Electrostatics", 2003, pp. 109-128, vol. 57, No. 2, Publisher: Elsevier, Published in: http://www.sciencedirect.com/science/article/pii/S0304388602001067.

L. Lomb et al., "Radiation damage in protein serial femtosecond crystallography using an x-ray free-electron laser", "Physical Review", 2011, pp. 2141111-2141116, vol. 84, No. 21, Publisher: American Physical Society, Published in: http://prb.aps.org/abstract/PRB/v84/i21/e214111.

Ioan Marginean et al., "Charge Reduction in Electrosprays: Slender Nanojets as Intermediates", "Journal of Physical Chemistry B", 2006, pp. 6397-6404, vol. 110, No. 12, Publisher: American Chemical Society, Published in: http://www.ncbi.nlm.nih.gov/pubmed/16553459.

Luis B. Modesto-Lopez et al., "Electrospray-assisted characterization and deposition of chlorosomes to fabricate a biomimetic light-harvesting device", "Energy and Environmental Science", 2010, pp. 216-222, vol. 3, Publisher: Royal Society of Chemistry, Published in: http://pubs.rsc.org/en/Content/ArticleLanding/2010/EE/b914758f.

J. O'Shea et al., "Electrospray deposition of carbon nanotubes in vacuum", "Nanotechnology", 2006, pp. 1-4, vol. 18, No. 3, Publisher: IOP Publishing, Published in: http://iopscience.iop.org/0957-4484/18/3/035707/.

A. Patriksson et al., "Protein Structures under Electrospray Conditions", "Biochemistry", 2007, pp. 933-945, vol. 46, No. 4, Publisher: American Chemical Society, Published in: http://pubs.acs.org/doi/abs/10.1021/bi061182y.

D. Shapiro et al., "Powder diffraction from a continuous microjet of submicrometer protein crystals", "Journal of Synchrotron Radiation", 2008, pp. 593-599, vol. 15, No. 6, Publisher: International Union of Crystallography, Published in: http://scripts.iucr.org/cgi-bin/paper?S0909049508024151.

R. Sierra et al., "Nanoflow electrospinning serial femtosecond crystallography", "Biological Crystallography", 2012, pp. 1584-1587, vol. 68, No. 11, Publisher: International Union of Crystallography, Published in: http://scripts.iucr.org/cgi-bin/paper?S0907444912038152.

Janine C. Swarbrick et al., "Electrospray deposition in vacuum", "Applied Surface Science", 2006, pp. 5622-5626, vol. 252, No. 15, Publisher: Elsevier, Published in: http://www.sciencedirect.com/science/article/pii/S0169433205016806.

A. Wortmann et al., "Shrinking Droplets in Electrospray Ionization and Their Influence on Chemical Equilibria", "Journal of the American Society for Mass Spectrometry", 2007, pp. 385-293, vol. 18, No. 3, Publisher: Springer Science and Business Media, Published in: http://www.zenobi.ethz.ch/publications/2007/wortman%20jasms%202007.pdf.

* cited by examiner

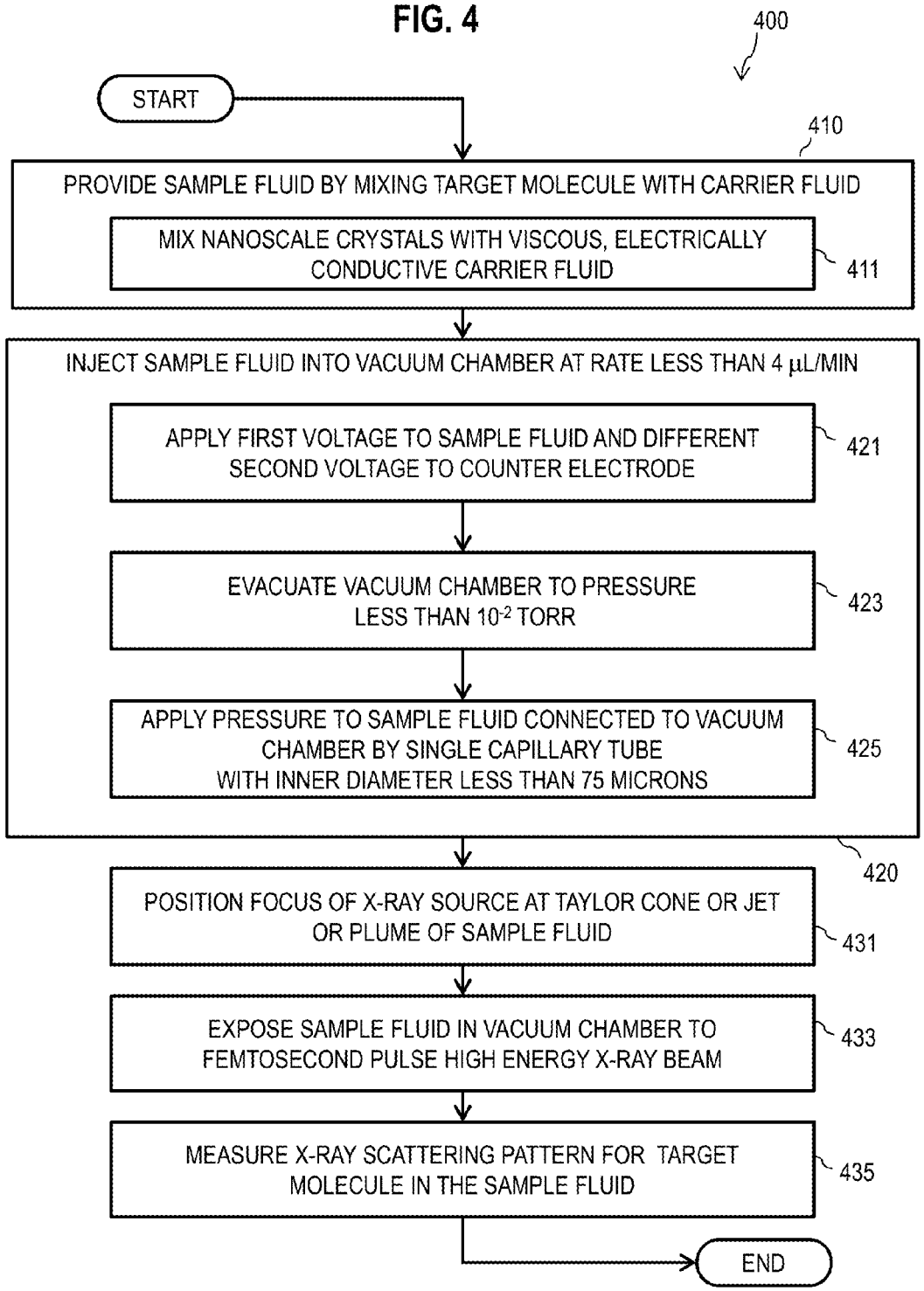

APPARATUS AND METHOD FOR NANOFLOW LIQUID JET AND SERIAL FEMTOSECOND X-RAY PROTEIN CRYSTALLOGRAPHY

STATEMENT OF GOVERNMENTAL INTEREST

This invention was made with Government support under contract DE-AC02-76SF00515 awarded by the Department of Energy. The Government has certain rights in the invention.

BACKGROUND OF THE INVENTION

Serial femtosecond (fs, $10^{-15}$ seconds) crystallography (SFX) using X-ray Free-Electron laser (XFEL) radiation is an emerging method for three dimensional (3D) structure determination that extracts structural information from nanometer (nm, $10^{-9}$ meters) to micron (micrometer, μm, $10^{-6}$ meters) sized crystals. This method relies upon intense X-ray pulses that are sufficiently short to pass through the sample before the onset of significant radiation damage (diffraction-before-destruction). SFX therefore promises to break the correlation between sample size, damage and resolution in structural biology. In this approach, a liquid microjet is used to introduce randomly oriented crystals into the XFEL beam. Structures with less than 2 Ångström (Å, 1 Å=$10^{-10}$ meters) resolution have been solved using the method. SFX is unique from standard crystallography in that particle sizes on the order of microns dispersed in aqueous solutions are used instead of a single large crystal (that takes months of method development to grow) mounted on a loop or grid. One known method to deliver sample to the x-ray interaction region is the Gas Dynamic Virtual Nozzle (GDVN, e.g., see Shapiro, Chapman et al. 2008, DePonte et al., 2008, 2009, 2011, and Ganon-Calvo et al., 2010). A thin liquid jet is formed from a highly pressurized liquid reservoir and a high pressure sheath gas flow from concentric capillary tubes. The thin jet is subjected to femtosecond X-ray pulses (e.g., see Barty, Caleman et al. 2011; Chapman, Fromme et al. 2011; Hunter, DePonte et al. 2011; Lomb, Barends et al. 2011; Aquila, Hunter et al. 2012; Johansson, Arnlund et al. 2012; Koopmann, Cupelli et al. 2012).

SUMMARY OF THE INVENTION

Though suitable for many purposes, the known method for sample delivery suffers from one or more of the following disadvantages determined by inventors: (1) high sample consumption rate compared to precious sample amounts; (2) sample settling in the reservoir or transfer lines prior to analysis; (3) fluctuation of jet position; and (4) use of gas sheath and metal shield surrounding the liquid jet in a vacuum chamber. Current sample consumption rates are typically 10 to 16 microliters (μl, 1 μl=$10^{-6}$ liters) per minute (min). Sample consumption rates of less than about one μl/min are desirable to enable analysis of precious biological samples. Sample settling reduces data collection rates and increases the likelihood of clogging. Stability of the jet position is desirable because of the small size of the jet (1 micron) and the X-ray focus (0.1-1 micron). Access to the jet unimpeded by differential pumping shrouds, gas sheath flows or other components is highly desirable for performing time resolved crystallography experiments, such as measurements at several points along the liquid jet and downstream droplet cloud.

Improvements are disclosed here that allow stable, low consumption rate, accessible liquid jet with nanoscale and microscale targets, such as molecules, nanometer sized crystals (nanocrystals), cells or organelles, in vacuum. Such a liquid jet is called herein a nanoflow liquid jet and is suitable for SFX as well as for nanoparticle synthesis, 'soft' ionization of biomacromolecules for mass spectrometry, thin film generation, high harmonic generation, and pharmaceutical delivery.

In a first set of embodiments, a method includes providing a sample fluid by mixing a plurality of a first target of interest with a carrier fluid. The method includes injecting the sample fluid into a vacuum chamber at a rate less than about 4 microliters per minute.

In another set of embodiments, an apparatus includes a pump configured to apply pressure to a sample fluid and a capillary tube of inner diameter less than 100 microns in fluid communication with the pump, wherein the capillary tube is open at a distal end. The apparatus also includes a voltage source configured to apply a first voltage to the sample fluid inside the capillary tube, and a counter electrode configured to be charged at a different second voltage. The counter electrode has a shape that is axially symmetric and has a first end closest to an axis of symmetry and a second edge farthest from the axis of symmetry. The distal end of the capillary and the counter electrode are configured to be disposed inside a vacuum chamber.

In another set of embodiments, a non-transitory computer-readable medium carries one or more sequences of instructions, wherein execution of the one or more sequences of instructions by one or more processors causes an apparatus to perform applying a first voltage to a sample fluid and a different second voltage to a counter electrode in a vacuum chamber. The apparatus is further caused to inject the sample fluid into the vacuum chamber at a rate less than about 4 microliters per minute.

Still other aspects, features, and advantages of the invention are readily apparent from the following detailed description simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 4 is flowchart that illustrates an example method, according to one embodiment;

DETAILED DESCRIPTION

Figure 1A:
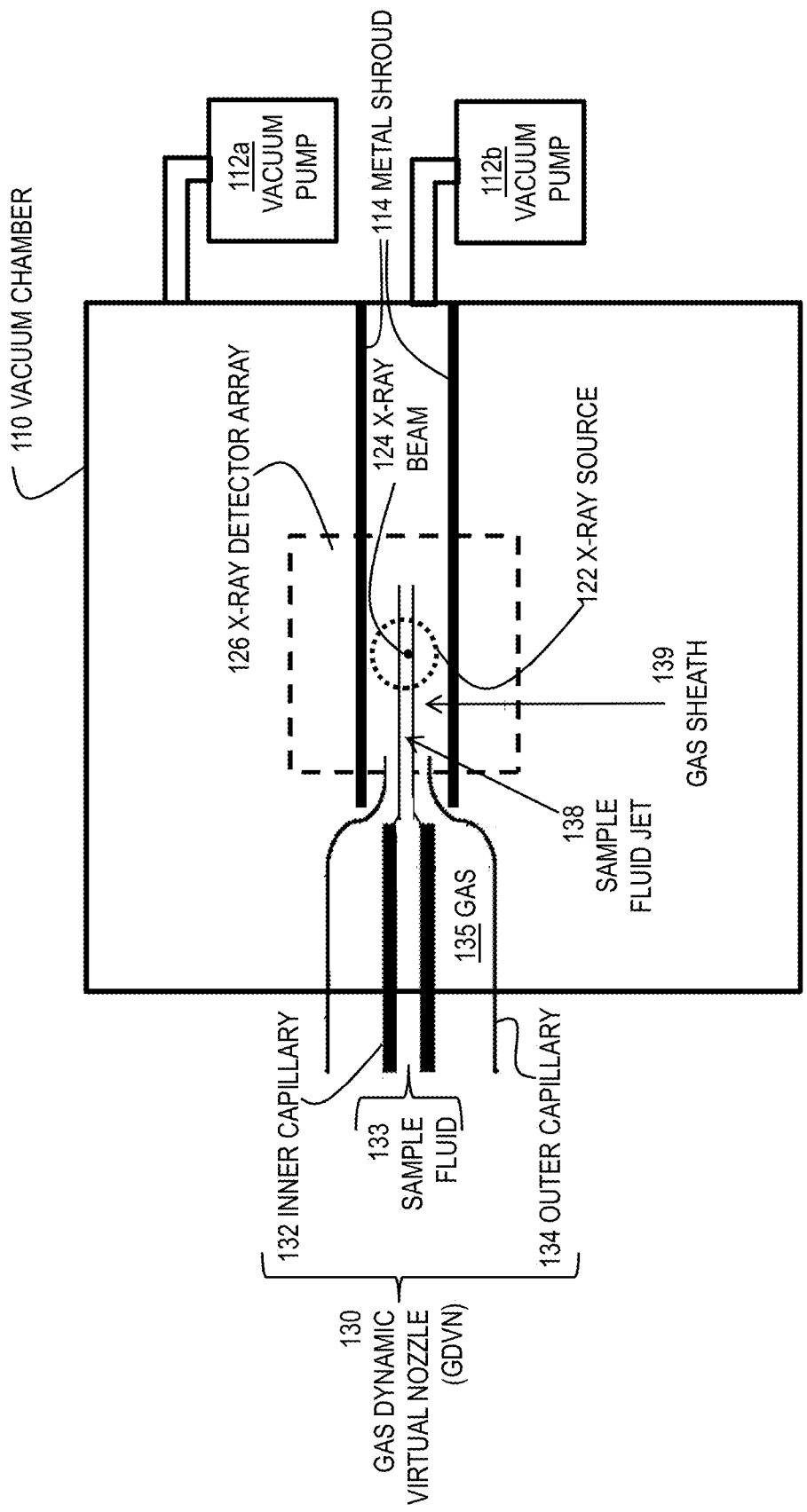
FIG. 1A is a block diagram that illustrates example use of gas dynamic virtual nozzle (GDVN) for serial femtosecond X-ray crystallography.

A method and apparatus are described for nanoflow liquid jet and serial femtosecond X-ray protein crystallography. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. Various references are cited herein, both above and in the following. The entire contents of the cited references are hereby incorporated by reference as if fully set forth herein, except for terminology that is inconsistent with the terminology used herein. As used herein, the following terms and abbreviations have the meanings given in Table. 1.

TABLE 1

| Terms and Definitions. | |
|---|---|
| Å | Ångström, 1 Å = $10^{-10}$ meters |
| centipoise | (symbol cP) is one one-hundredth of a poise |
| CXI | Coherent X-ray Imaging endstation of LCLS |
| DNA | Deoxyribonucleic acid - a double helix comprising two complementary sequences of nucleotide bases (each selected from a set of four nucleotides: adenine, thymine, cytosine, and guanine, represented by the letters A, T, C and G, respectively) |
| electrospinning | a variation of electrospray in which viscous solutes are used to overcome the charge repulsion that forms the electrospray and a thin liquid jet is formed instead. This process has found use in polymeric nanofiber manufacturing. Conventionally not done in vacuo. |
| electrospray | electrohydrodynamic atomization widely applied in nanoparticle synthesis, 'soft' ionization of biomacromolecules for mass spectrometry, thin film generation, and pharmaceutical delivery. Occurs at the exit of an open-ended capillary filled with a conductive liquid when exposed to an electric field of appropriate strength. Conventionally not done in vacuo. |
| fs | femtosecond, 1 fs = $10^{-15}$ seconds. |
| GDVN | Gas Dynamic Virtual Nozzle - process to provide a fluid jet using high pressure and a gas sheath flow. |
| LCLS | Linac Coherent Light Source at SLAC National Accelerator Laboratory, Menlo Park, CA |
| ml | milliliter, 1 ml = $10^{-3}$ Liters |
| nm | nanometer, 1 nm = $10^{-9}$ meters |
| parameter | A term in an equation that is constant for a particular application or context, but can vary among different applications or contexts. |
| PDB | Protein Data Bank |
| PEG | polyethylene glycol |
| peptide | also called a protein fragment, a molecule comprising multiple amino acids, typically a shorter sequence of amino acids than a protein, |
| poise | (symbol P) is the unit of dynamic viscosity in the centimeter gram second (cgs) system of units and is equal to 1 gram per second per centimeter. |
| protein | A molecule comprising a long sequence of amino acids, selected from a set of 22 amino acids in humans. |
| PS II | Photosystem II, a protein responsible for oxidation of water using light from the sun. The light-driven, four-photon reaction is catalyzed by a $Mn_4CaO_5$ cluster located at a lumenal side of PS II. |

TABLE 1-continued

Terms and Definitions.

| | |
|---|---|
| RNA | Ribonucleic acid - a molecule comprising a single sequence of nucleotide bases (each selected from a set of four nucleotides: adenine, uracil, cytosine, and guanine, represented by the letters A, U, C and G. |
| SFX | serial femtosecond crystallography, a process to determine atomic structure of molecules flowing past an high photon energy X-ray source that emits femtosecond pulses, which produces a series of X-ray scattering patterns |
| siemens | one siemens is equal to the reciprocal of one ohm, and is also referred to as the mho, and is a measure of electrical conductivity (reciprocal of resistance) and electrical admittance (reciprocal of impedance) |
| viscosity | a measure of the resistance of a fluid which is being deformed by either shear or tensile stress, such as a proportionality factor between a force applied per unit area of a fluid and resulting velocity gradient perpendicular to that area. |
| variable | a term in an equation that can assume multiple different values for a single application or context. |
| XFEL | X-ray Free-Electron laser radiation, based on using a relativistic electron beam as the lasing medium which moves freely through a magnetic structure, hence the term "free electron." The free-electron laser has the widest frequency range of any laser type, and can be widely tunable to include very high frequency (high photon energy) X-rays. |
| μl | microliter, 1 μl = $10^{-6}$ Liters |
| μm | micrometer, also called a micron, 1 μm = $10^{-6}$ meters |

Some embodiments of the invention are described below in the context of serial femtosecond X-ray crystallography (SFX) of protein nanocrystals. However, the invention is not limited to this context. In other embodiments, filtered or unfiltered nanocrystals of other molecules, cells, viruses, organelles such as carboxysomes or single molecules are included in the sample fluid, or nanoflow liquid jet is used for one or more other purposes, such as nanoparticle synthesis, 'soft' ionization of biomacromolecules for mass spectrometry, thin film generation, high harmonic generation, and pharmaceutical delivery. In other embodiments, additional detection schemes can be used to probe the interaction of the X-ray pulse with the injected sample, such as analyzers used for spectroscopy or time-of-flight mass spectrometry. One or more of such detectors can be used separately or in parallel with the X-ray scattering detector. In other embodiments, synchrotron radiation or laser pulses from table-top lasers systems of any available wavelength are used. For the latter, synchronized timing with XFEL pulses can provide the means to make movies of molecular processes, perhaps even to femtosecond resolution, where the optical pulse pumps the molecules in a crystal and the X-rays probe the structure. In other embodiments, the molecules of interest are mixed with a reactant a known distance from the interaction region to provide study of chemical kinetics.

In the work presented here, solvent properties, such as 30% glycerol/10% polyethylene glycol (PEG), or 10% PEG/1.4 molar (M) sucrose in water, have been discovered for stable electrospinning in vacuo. Furthermore, it has been discovered that nanocrystals can be delivered in a one micron diameter jet in vacuo. These discoveries provide a new nanoflow source suitable for serial femtosecond crystallography (SFX) among other processes. These techniques for electrospinning in vacuo have opened the application of SFX to a much wider array of biological materials because it consumes about 50 times less sample than the current method based on GDVN. Furthermore, these techniques provide other advantages, such as the reduction of settling, the removal of a gas sheath that contaminates the x-ray scattering, and the removal of a metal shroud that limits the locations along the flow-focused liquid jet of GDVN where measurements can be made. In the work presented here, measurements can even be made inside the Taylor cone, providing typically a 50 micron (dependent on capillary inner diameter) X-ray path length through the sample.

Figures 1B, 1C, 1D, 1E:
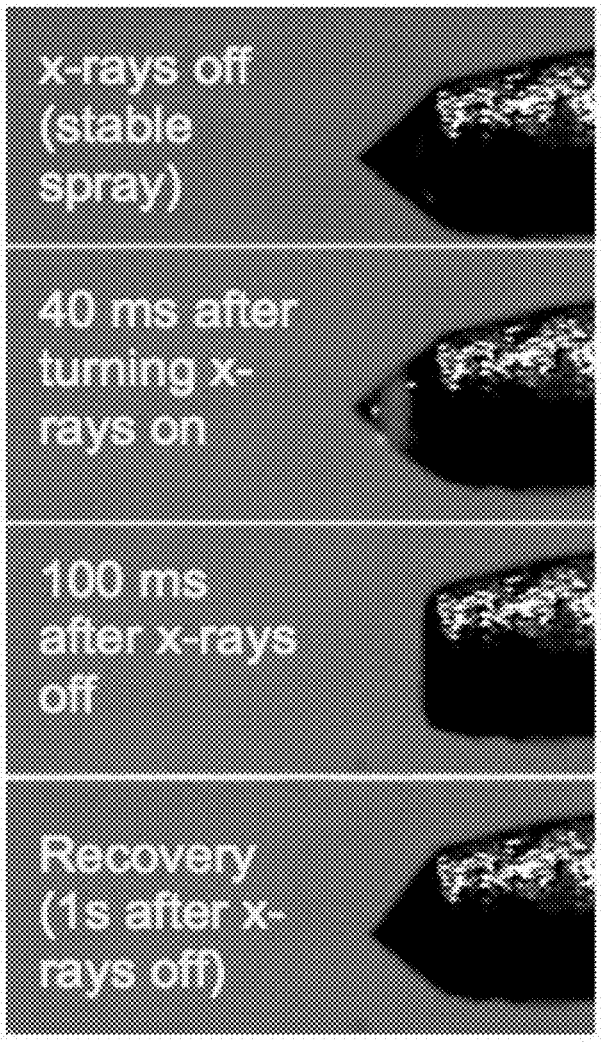
FIG. 1B through FIG. 1E are photographs that illustrate breakdown of electrospray under exposure to x-rays at atmospheric pressures.

FIG. 1 is a block diagram that illustrates example use of a gas dynamic virtual nozzle (GDVN) 130 for serial femtosecond X-ray crystallography. The GDVN 130 includes an inner capillary 132 and an outer capillary 134. Sample fluid 133 is forced through the inner capillary 132 under pressure, while a gas 135 is forced through the outer capillary 134 under pressure. The result is a sample fluid jet 138 surrounded and focused by a gas sheath flow 139. To reduce the gas load in a vacuum chamber 110, a metal shroud 114 surrounds the gas sheath 139 and is differentially evacuated. For example, one low pressure vacuum is maintained outside the metal shroud by a first vacuum pump 112a while a higher pressure vacuum is maintained inside the metal shroud by a second vacuum pump 112b.

When used for SFX, the sample fluid jet 138 is illuminated by an X-ray beam 124 from X-ray source 122 and the scattered emissions (photons) are recorded at an X-ray detector array 126. The incident and scattered X-rays pass through ports in the metal shroud 114. A disadvantage of this arrangement is that the position of the sample fluid jet 138 fluctuates so that the ports are not always ideally aligned. Also, the presence of the metal shroud 114 makes it difficult to measure the X-ray scattering at multiple different distances along the sample fluid jet 138 and the valuable high angle scattering from the sample can be shadowed from the detector array 126. Furthermore, the X-ray scattering, even through the ports, is affected by the presence of the gas sheath flow 139. In addition, target molecules in the low viscosity sample fluid tend to settle out in one or more pumps or reservoirs before reaching the GDVN 130, causing the target molecules to be more sparse in the sample fluid jet, and, thus, reducing the number of useful measurements from the X-ray beam 124.

Electrospray was attempted to circumvent the limitations of GDVN. Unexpectedly, it was observed that the synchrotron radiation severely perturbs the electrospray. Powder diffraction from crystal suspensions delivered to synchrotron radiation by GDVN has been recorded (Shapiro, Chapman et al. 2008). An attempt to repeat this experiment on crystals passing through the Taylor cone of an electrospray source at atmospheric pressure was performed at the Swiss Light Source cSAXS beamline using a fully closed gap configuration of the U19 undulator (4.6 mm) and 8 kilo-electron Volts (keV, 1 keV=$10^3$ electron Volts) X-rays focused into n approximately 5 micron×20 micron (100 square micron) footprint containing up to $10^{12}$ photons/second. FIG. 1B through FIG. 1E are photographs that illustrate breakdown of electrospray from a 100 micron outer diameter capillary under exposure to X-rays at atmospheric pressures, before during and after exposure to synchrotron radiation. The result is that only the leading edge of the X-rays interacts with the electrospray. The Taylor cone compresses in less than 100 milliseconds (ms, 1 ms=$10^{-3}$ seconds) and does not return until about 1000 ms after a shutter of the X-ray source is closed. Thus no signal can be recorded from the electrospray after a time less than about 40 ms. These measurements show evidence that the destabilization occurs on a timescale shorter than about 10 ms, as the use of 10 ms exposures did not result in any detectable signals. It was concluded that rapid gas ionization by the incoming X-ray pulse destabilizes the electrospray and precludes the use of synchrotrons to probe the structure and dynamics of electrosprays and the particles within them.

Use of the LCLS X-ray laser alleviates this shortcoming by providing ultrabright and ultrashort X-ray pulses that pass through the electrospray before it is destabilized by gas ionization. The plasma created by the beam breaks down and recombines on the scale of microseconds, enabling probing of an electrospray operating at atmospheric pressure with a repetition rate of 1 Hz. It is suspected that the physical reformation of the Taylor cone is the rate limiting process. However, another unexpected problem was that geometrical constraints of the large X-ray beam path at CXI caused background scattering from the high concentration of gas molecules. This background scattering precluded recording of crystalline Bragg diffraction.

Thus, it was observed that atmospheric pressure electrosprays cannot be probed with synchrotron radiation without severe perturbations. X-rays lasers can probe electrosprays at atmospheric pressure with 1 Hz repetition rate, limited by the electrospray re-stabilization but suffer from background scattering by surrounding gas molecules.

Electrospun liquid jets of protein crystals in vacuo can be made to similar dimensions as liquid jets created using a gas dynamic virtual nozzle and provide a complementary sample delivery mechanism for SFX using X-ray lasers. However, without cryoprotectant added to carrier fluids, the jet breaks down due to freezing; and, the GDVN must be used, with all its limitations.

To reduce background scattering, conditions were determined for stable electrospray in vacuo absent a gas sheath. Glycerol was added as a cryoprotectant to overcome the limitation of immediate freezing at the capillary exit. Studies of glycerol electrosprays in vacuo have shown high stability at <0.01 torr (1 torr=approximately 1.316×$10^{-3}$ atmosphere or 133.3 pascals, where 1 pascal is the SI units for pressure, one newton per square meter) (Ku and Kim 2003). Glycerol is also commonly used in crystal screens and as a cryoprotectant in synchrotron protein crystallography. Glycerol solutions of 25-30% by volume were discovered to be most effective. Highly viscous glycerol added a surprising extra advantage for SFX experiments by reducing the settling rate of crystals. Suspensions of crystals of sizes less than about 2 micron were stable for more than 12 hours. Similar to electrospray of solutions of pure glycerol, electrospun jets of crystal suspensions showed highest stability at pressures less than about 0.01 Torr.

Figure 2A:
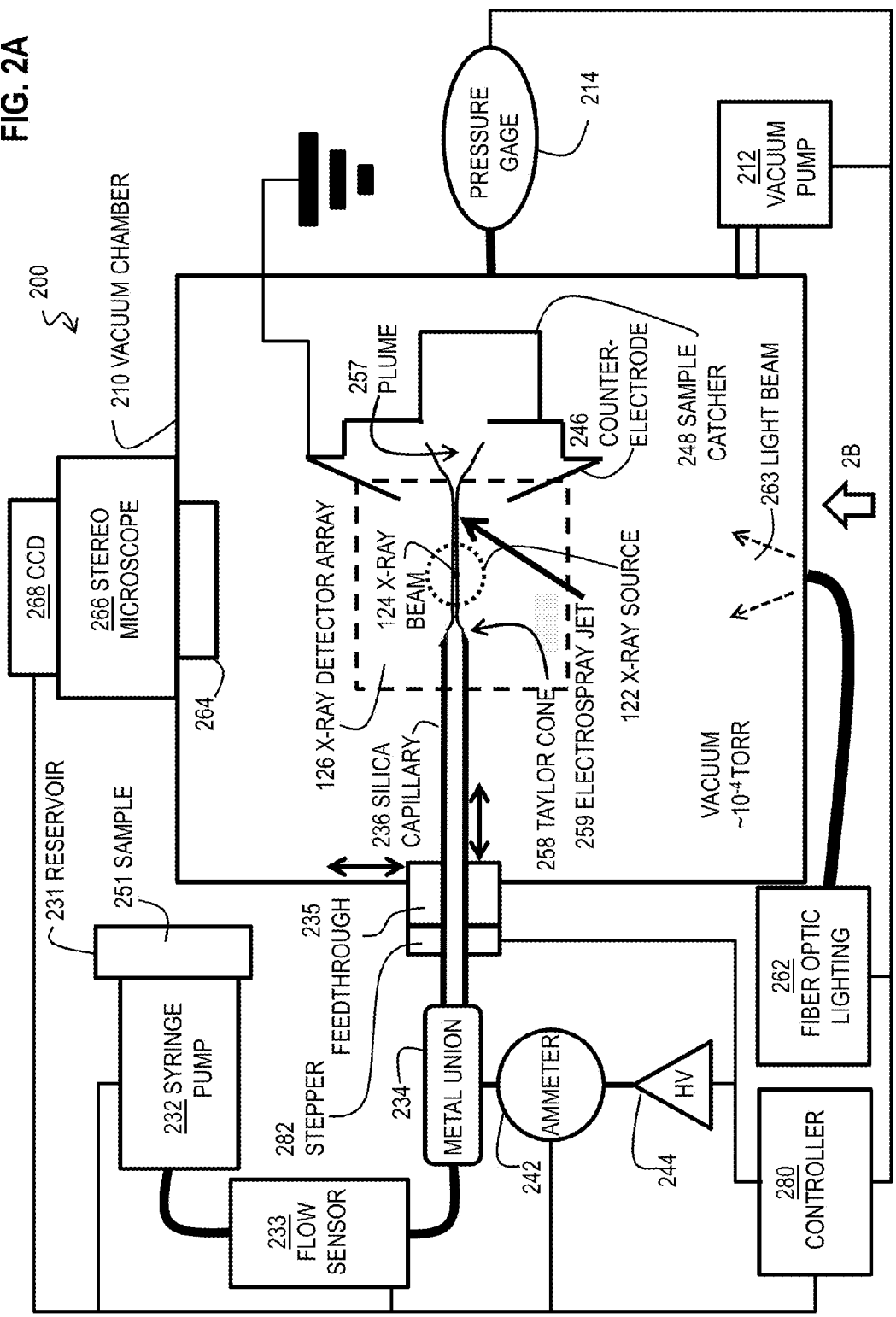
FIG. 2A and FIG. 2B are block diagrams that illustrate two views of an example apparatus for performing and testing nanoflow serial femtosecond X-ray protein crystallography, according to an embodiment.
Figure 2B:
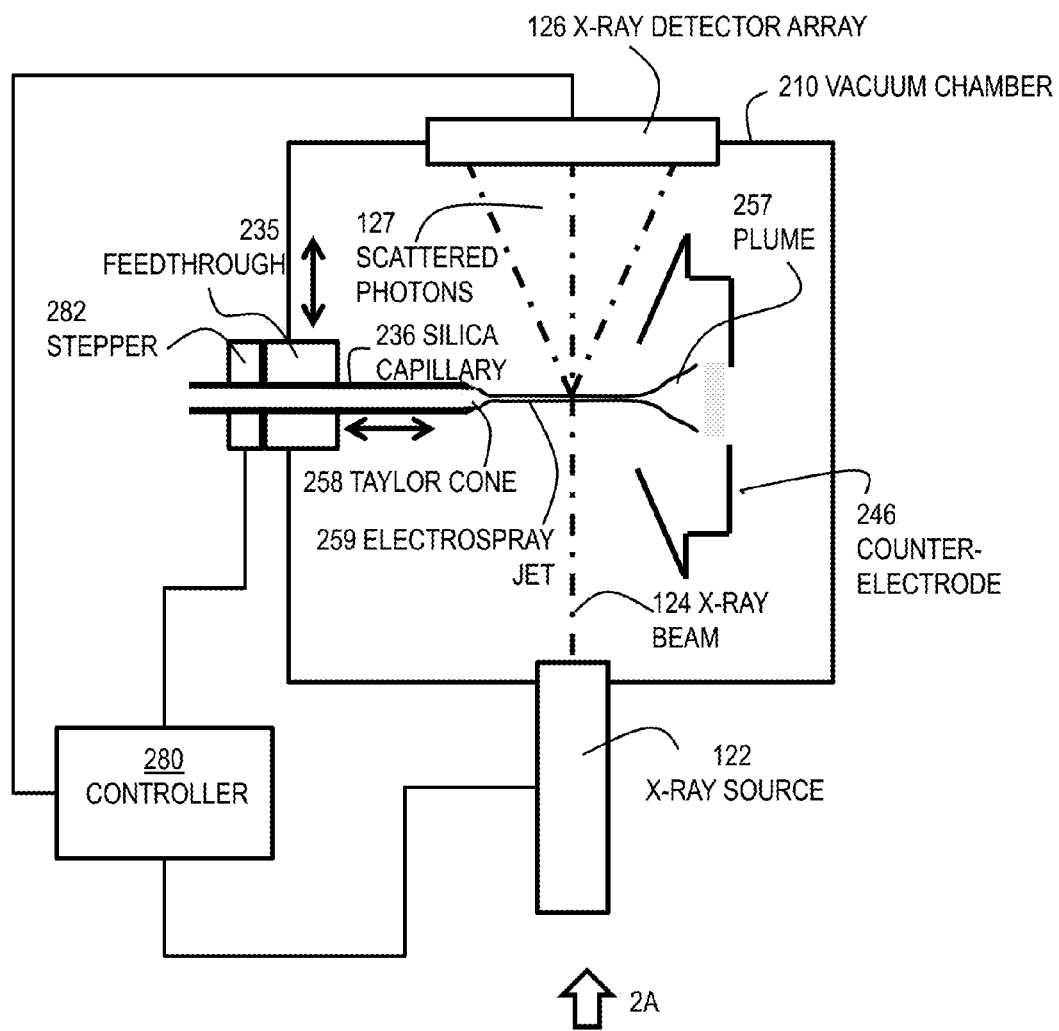

FIG. 2A and FIG. 2B are block diagrams that illustrates two views of an example apparatus 200 for performing and testing nanoflow liquid jet serial femtosecond X-ray protein crystallography, according to an embodiment. The apparatus includes a reservoir 231 for holding a sample 251, such as a mixture of nanocrystals with a viscous electrically conductive carrier fluid, as described in more detail below. In some embodiments, the apparatus includes an inline mixing apparatus to create the sample fluid from the molecules of interest and the carrier fluid, i.e. a simple T junction or more complex concentric flow apparatus. The reservoir is in fluid communication with a source of fluid pressure, such as syringe pump 232 that is in fluid communication with a capillary tube, such as silica capillary 236 with tapered open end. The pump 232 induces flow through an open distal end of the capillary tube. In the illustrated embodiment, the apparatus includes fluid flow sensor 233 configured to measure the rate of flow through the capillary tube. In another embodiment, pressure (10-50 pounds per square inch, psi, 1 psi=about 51.7 torr,) can be applied to a sample reservoir, with which the silica capillary 236 is in fluid communication, to induce flow through to the open distal end without any connectors. This embodiment is advantageous for minimizing potential for clogging due to crystal accumulation at a connector.

For electrospinning, the fluid is charged by a high voltage (HV) source 244, such as a Stanford Research Systems 0-5 kiloVolt (kV, 1 kV=$10^3$ volts) or 10 kV power supply, connected to a metal union component 234 that transfers the voltage applied to a metal vessel to a conducting fluid, such as the sample fluid, contained in the vessel. The electrical current, in picoamperes (pA, 1 pA=$10^{-12}$ Amperes), which flows into the fluid to maintain the voltage is measured by an ammeter 242. A counter electrode 246 is charged to a different voltage, e.g. to electrical ground in the illustrated embodiment. An opening in the proximal end of the counter electrode allows the flow of sample fluid to be collected neatly in a sample catcher 248 after passing the counter electrode 246.

Figure 2C:
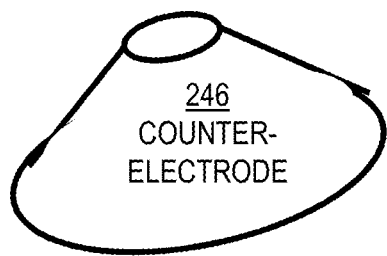
FIG. 2C and FIG. 2D are diagrams that illustrate a conical counter electrode with apex removed in oblique and plan views, respectively, according to an embodiment.
Figure 2D:
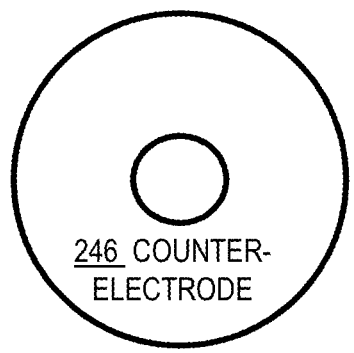
Figure 2E:
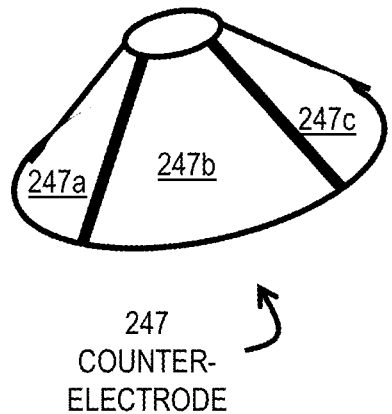
FIG. 2E and FIG. 2F are block diagrams that illustrate a quad-electrode conical counter electrode with apex removed in oblique and plan views, respectively, according to an embodiment.
Figure 2F:
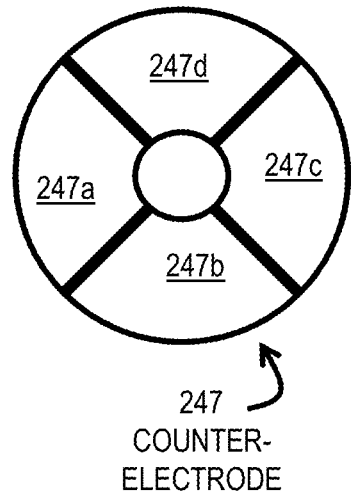

In the illustrated embodiment, the counter electrode is shaped as a cone with it apex removed, as depicted in FIG. 2C and FIG. 2D. FIG. 2C and FIG. 2D are block diagrams that illustrate a conical counter electrode with apex removed in oblique and plan views, respectively, according to an embodiment. That is, the counter electrode 246 has a shape that is axially symmetric and has a first end closest to an axis of symmetry and a second edge farthest from the axis. In some embodiments, the counter electrode has a more complex structure with multiple electrodes and multiple voltages. For example a segmented quad-electrode 247, depicted in FIG. 2E and FIG. 2F with four segments 247a through 247d, respectively, making up the cone, each separately chargeable, would enable steering functionality. FIG. 2E and FIG. 2F are block diagrams that illustrate a quad-electrode conical counter electrode 247 with apex removed in oblique and plan views, respectively, according to an embodiment.

The counter electrode 246 (or 247) is disposed with the axis aligned with the flow of the sample fluid (e.g., the center of the capillary tube) and with the first edge closer than the second edge to an injection point at the open distal end of the capillary, e.g., silica capillary 236 where the sample fluid is injected toward the counter electrode 246. The electrospray forms a Taylor cone 258 downstream of the distal end of capillary 236 followed by an electrospray jet 259 and, in some embodiments, a plume 257. Tapering the distal open end of the capillary tube offers the advantage of enhancing formation of the Taylor cone 258.

For electrospinning in vacuo, the capillary, e.g., silica capillary 236, is passed into a vacuum chamber 210 through a feedthrough fitting 235, such as a 1/16" Swagelok fitting. In some embodiments, the capillary tube was fixed to a stepper 282, such as an XYZ nanopositioning stage, to enable positioning of the tube distal end, and the jet emanating from it, relative to other components in the vacuum chamber 210, as indicated by the double arrows in two dimensions. Vacuum pressures of about $10^{-4}$ torr are achieved by the vacuum pump 212. In various embodiments, the vacuum pressure is in a range from about $10^{-5}$ torr to about $10^{-2}$ torr. The vacuum pressure is monitored by pressure gauge 214. The counter electrode 246 is disposed in the vacuum chamber with the axis aligned with the flow of the sample fluid in the vacuum chamber and with the first edge closer than the second edge to an injection point at the distal end of capillary 136 where the sample fluid is injected into the vacuum chamber.

To visualize the electrospray, in some embodiments, a light source, such as fiber optic lighting source 262 emits a light beam, e.g. light beam 263, into the vacuum chamber 210. In various other embodiments, an in-vacuum LED or in-vacuum pulsed laser acts as the light source. The transmitted light is detected at a video camera, such as formed by lenses 264, stereomicroscope 266, and charge coupled device (CCD) array 268. In some embodiments, the electro spray is not visualized, and one or more of components 264, 266 and 268 are omitted.

For SFX applications within vacuum chamber 210, an X-ray source 122, such as a XFEL, emits an X-ray beam 124, such as serial femto second pulse X-ray beam, that intersects the electrospray, such as along electrospray jet 259. Intersection of the X-ray beam 124 is controlled by stepper 282 moving the distal end so that the beam intersects at different portion of the fluid flow, either at Taylor cone 258 or jet 259 or plume 257. Scattered X-ray photons are detected at the x-ray detector array 126.

Figure 12:
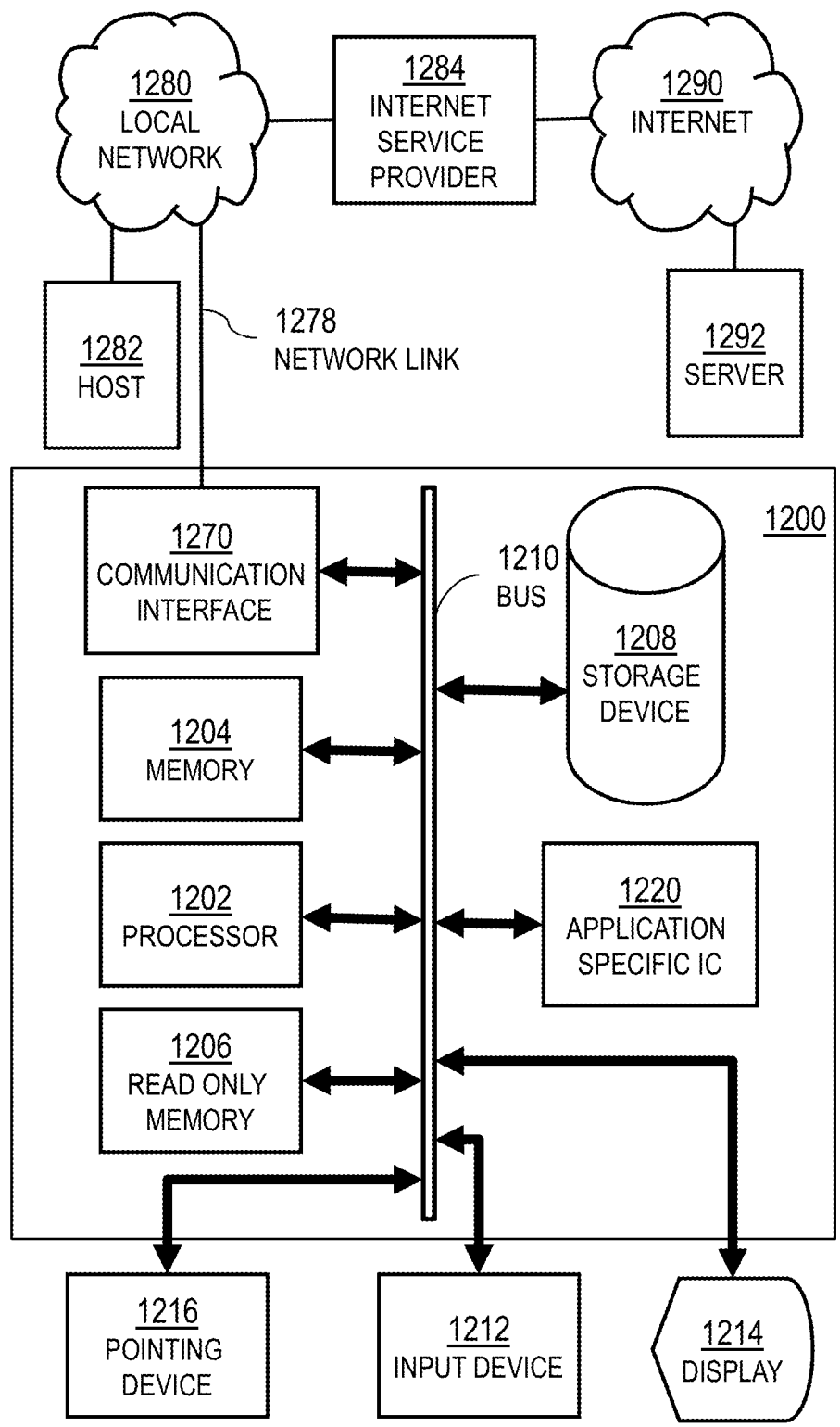
FIG. 12 is a block diagram that illustrates a computer system upon which an embodiment of the invention may be implemented.
Figure 13:
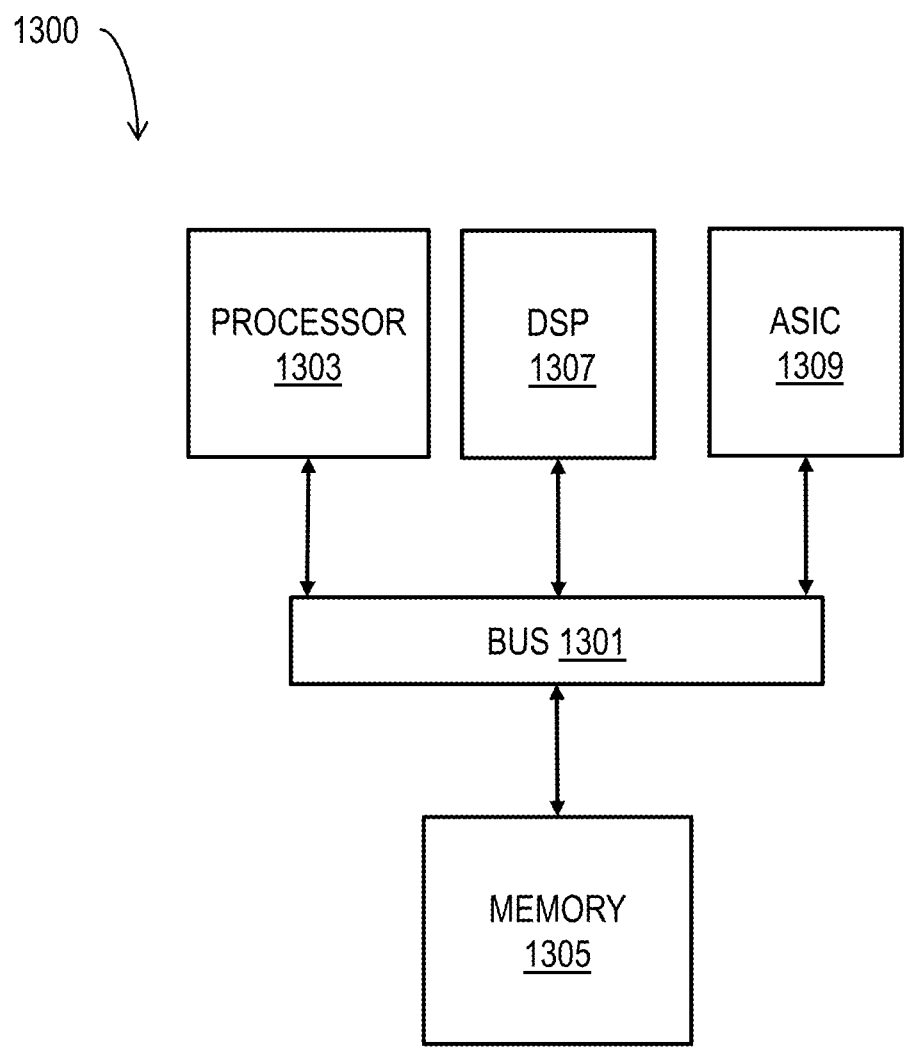
FIG. 13 illustrates a chip set upon which an embodiment of the invention may be implemented.

In some embodiments, a controller 280 is included to control one or more of syringe pump 232, high voltage source 244, fiber optic lighting source 262, vacuum pump 212 and X-ray source 122. In some embodiments the controller also receives or stores output, or both, from one or more of flow sensor 233, ammeter 242, pressure gauge 214, and CCD array 268. In various embodiments, the controller 280 comprises one or more computer systems as depicted in FIG. 12 or chip sets as depicted in FIG. 13, or some combination. FIG. 2B depicts a perpendicular view in the direction indicated by the arrow labeled 2B.

In FIG. 2B, vacuum chamber 210, stepper 282, feedthrough 235, capillary 236, Taylor cone 258, electrospray jet 259, plume 257, counter electrode 246 and controller 280 are as described above. Apparent in this view are the X-ray source 122 and X-ray detector array 126, as well as the X-ray beam 124, also included in FIG. 2A and described above. Here, also shown, are Bragg scattered X-ray photons 127 not previously depicted.

The nanoscale dimensions of electrosprays, in particular the jet filament and the submicrometer droplet size distribution, have never been measured in situ because typical light scattering techniques cannot be extended to this scale (Smith, Flagan et al. 2002; Wortmann, Kistler-Momotova et al. 2007). However, the perturbation of biological materials transiting within these nanoscale electrospray regions has received recent interest because of the growth in applications of electrosprays to the characterization and preparation of biological materials. For example, tobacco mosaic virus has been shown to collapse during the electrospray process (Allmaier, Laschober et al. 2008) and the viability of bacteriophages is known to vary with applied electrospray voltage (Jung, Lee et al. 2009). Currently, the point during the electrospray process at which these changes in biomaterial structure are induced is not known. Insights into these structural perturbations are important to optimize electrospray delivery of biological materials to surfaces for applications such as biomimetic solar cell manufacture (Modesto-Lopez, Thimsen et al. 2009), injection into vacuum for mass spectrometry (Patriksson, Marklund et al. 2007) and single molecule x-ray diffractive imaging applications (Bogan, Benner et al. 2008; Bogan, Boutet et al. 2009)

SFX provides an opportunity to determine structural changes at various positions along the electrospray by measuring X-ray diffraction from materials inside of electrosprays. Due to the anatomy of an electrospray, signal changes are expected to be measured based on the position along the electrospray where the X-rays probe, and any structural changes induced in the target biomolecule.

Figure 3:
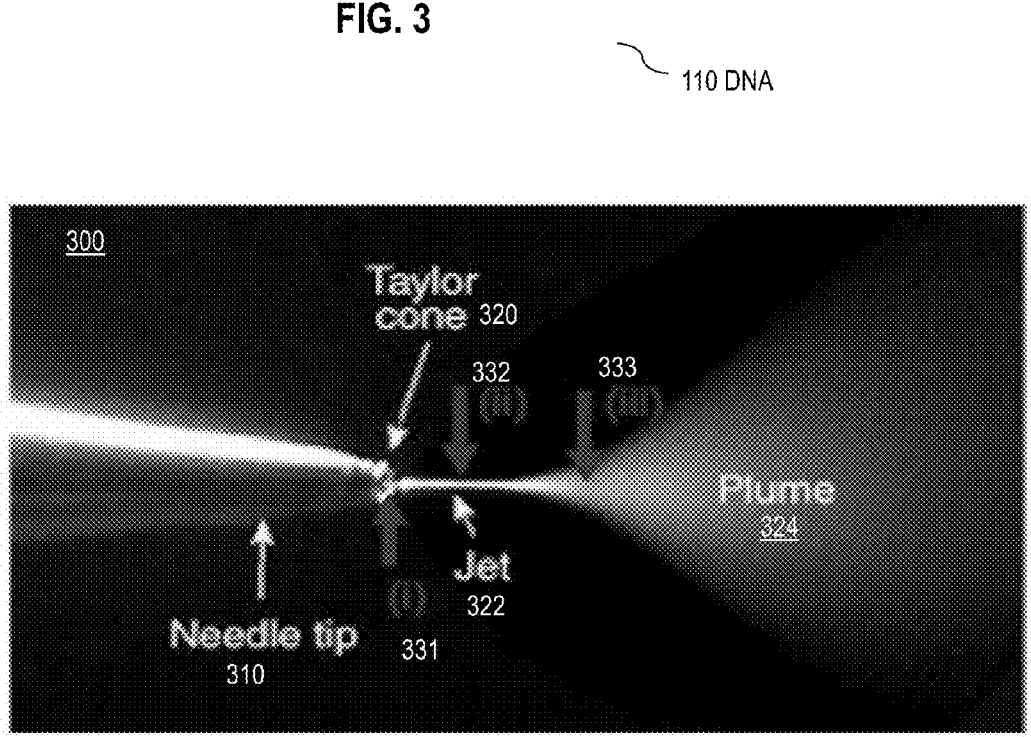
FIG. 3 is a photograph that illustrates example nanoflow liquid jet produced by apparatus of FIG. 2, according to an embodiment.

FIG. 3 is a photograph 300 that illustrates example electrospray produced by apparatus of FIG. 2, according to an embodiment. Evident is a distal end of a capillary tube, labeled a "needle tip" 310 in FIG. 3, from which is extruded a Taylor cone 320, a jet 322 and a plume 324. In various embodiments, X-ray scattering measurements are made at position 331 in Taylor cone 320, position 332 in jet 322 or at position 333 at a base of plume 324.

Strong signals are expected from materials inside of the electrospray capillary at position 331 just outside the needle tip 310 in an experiment identical to Small-angle X-ray scattering (SAXS) measurements on liquids flowing through capillaries. In this position, the sample volume, $\sim 2\times10^{-8}$ $cm^3$, is defined by the capillary diameter (50 μm) and the beam size (20 μm). For a solution of proteins with $10^{12}$ particles per ml, this corresponds to 20,000 proteins in the exposure volume at any one instant. In position 332 of the jet 322, materials are concentrated in space into a small filament of liquid <1 μm in diameter. Here the sample volume is $\sim 2\times10^{-11}$ $cm^3$. The highly confined sample region is ideally suitable for delivery of sample to the future submicron focus of LCLS and other XFELs. In the plume 324, materials are divided into primary electrospray droplets 200-400 nm in diameter that are dispersed over a large volume, 100-1000 μm in diameter. It was expected that the expansion of the liquid into 20-200 times the original volume would require even longer integration times for adequate signal-to-noise ratios. At position 333, conformational changes may be observed in the biomolecules as they transition into the gas phase.

Thus, there is interest in all three electrospray regions, including the Taylor cone 320 in the immediate vicinity of the nozzle tip, the thin electrostatic jet 322 emerging from the tip of the Taylor cone, and the plume 324 of fine droplets formed by Coulombic explosion in the jet. The conformation of several classes of biological particles (ranging from single proteins to larger macromolecular aggregates or crystals) can be characterized by x-ray scattering in an attempt to monitor conformational changes that occur during electrospray process. Analysis of the scattered intensity allows the study of particle dynamics in electrospray, such as hydrodynamic alignment, and structural modification of biological molecules caused by interaction with strong electric field, water shell evaporation and potentially even biological ion evaporation from the nanoscale droplets, a phenomenon predicted to occur on a picosecond (ps, 1 ps=$10^{-12}$ seconds) timescale (see, e.g., Marginean, Znamenskiy et al. 2006). The thin jet region is of particular interest for SFX since the jet can be used for nanocrystal delivery.

FIG. 4 is flowchart that illustrates an example method 400 for generating nanoflow liquid jet and serial femtosecond x-ray protein crystallography, according to one embodiment. Although steps are depicted as integral blocks in a particular order for purposes of illustration, in other embodiments, one or more steps or portions thereof are performed in a different order, or overlapping in time in series or parallel, or are omitted, or one or more steps are added, or the method is changes in some combination of ways.

In step 410 a sample fluid is prepared by mixing multiple copies of a target of interest, such as a molecule, crystal, cell or organelle of interest, with a carrier fluid. Thus, step 410 provides a sample fluid by mixing a plurality of a first target of interest with a carrier fluid. In some embodiments, about $10^9$ copies of a target molecule are included per milliliter of sample fluid. In some embodiments, step 410 includes step 411, in which nanoscale crystals are mixed with a viscous, electrically conductive carrier fluid, with conductivity similar to fluids used in well-known electrospray operation. Experimental embodiments included conductivities in a range of from about 0.5 to about 5 milliSiemens per centimeter (mS/cm, 1 milliSiemen, mS, $=10^{-3}$ Siemens, 1 centimeter, cm, $=10^{-2}$ meters). It was determined that below a value of approximately 0.5 mS/cm, the form of the electrospray starts suffering which requires higher and higher voltages which leads to the jet beginimg to suffer and fail. In some of these embodiments, about $10^9$ nanocrystals of the target molecule are included per milliliter of sample fluid. Thus, in some embodiments, providing the sample fluid further comprises providing the sample fluid by mixing a plurality of nanoscale crystals of the first target of interest with the carrier fluid. In some embodiments, the nanoscale crystals are each smaller than about 500 nanometers in a largest dimension. In various embodiments, crystals of sizes from 0.2 microns to 20 micron have been measured at LCLS. In some embodiments, the viscosity of the carrier fluid is in a range from about 3 centipoise (cP) to about 5 cP. For example, in some embodiments, the carrier fluid comprises 30% by volume glycerol and 10% by volume polyethylene glycol (PEG) 2000.

In step 420, the sample fluid is injected into a vacuum chamber at a rate less than about 4 microliters per minute, a rate that is a lower than is achievable with GDVN. In some embodiments, the injection rate is preferably even lower, at less than 1 microliters per minute. In some embodiments, the injection rate is about 0.1 to 0.5 microliters per minute. At about 0.3 microliters per minute, the target molecules or nanocrystals passes an x-ray focus at a rate of about 5000 per second.

In an illustrated embodiment, such nanoflow is achieved by steps 421, 423 and 425. In step 421, a first voltage is applied to the sample fluid, e.g., at a fluid electrode such as metal union 234 or an electrode in contact with the sample reservoir, and a different second voltage is applied to the counter electrode 246. In various embodiments, 1.7 kilovolts (kV, 1 kV=$10^3$ volts) to 5 kV are applied to one electrode and 0 to −5 kV applied to the other. For example, some embodiments operate with +2.3 kV in solution and −0.3 kV on the counter electrode and 6 millimeters (mm, 1 mm=$10^{-3}$ meters) to 8 mm distance between capillary and the counter electrode. In other embodiments, voltages are inverted to operate in negative mode electrospinning.

In step 423, the vacuum chamber is evacuated to a pressure less than about $10^{-2}$ Torr. Stable jetting is not observed at intermediate pressures above this level and below atmospheric pressure, consistent with prior work on pure glycerol and solat-doped glycerol solutions (e.g., see Ku, B. K. & Kim, 2003). In step 425, pressure is applied to the sample fluid connected to the vacuum chamber by the single capillary tube, e.g., pressure is applied by syringe pump 232 in fluid communication with silica capillary 236.

In various embodiments, the capillary tube has an inner diameter (ID) less than or equal to about 150 μm. For example, the fluid is injected through a single silicon capillary tube of ID about 50 microns to 150 microns ID, with both tapered and non-tapered distal end exits. Smaller capillaries are available commercially down to 5 micron inner diameter. Smaller capillaries lead to decreased flow rate and sample consumption but this is offset by increased likelihood for clogging. Capillaries smaller than 50 micron ID are most successful with pre-filtered solutions of less than 2 micron crystals, preferably less than 500 nm crystals In some embodiment, the sample fluid in the vacuum forms a jet less than about one micron in diameter.

In various embodiments, the vacuum chamber does not include a shroud to separate the vacuum chamber into two or more volumes pumped to different vacuum pressures as in a GDVN. In various embodiments, applied pressure injects the sample fluid into the vacuum chamber through a single silicon capillary tube without a sheath fluid flow introduced through a second concentric capillary tube as in a GDVN.

In step 431, the focus of the X-ray source is positioned in the electrospray, for example, using nanoscale stepping motors 282 attached to the capillary 236 or feedthrough 235. In step 433, the sample fluid is exposed to the X-ray beam, such as femtosecond pulse high energy x-ray beams from XFEL source at Linac Coherent Light Source's (LCLS) Coherent X-ray Imaging (CXI) endstation. Thus, step 433 includes exposing a portion of the sample fluid in the vacuum chamber to a femtosecond pulse high energy X-ray beam. For example, measurements are made at 120 femtosecond pulses per second. In step 435, the X-ray scattering is measured from each target molecule, or a nanocrystal of multiple copies of the target molecule, e.g., at an X-ray detector array. Thus step 435 includes measuring at an X-ray detector array an X-ray scattering pattern for the first target in the sample fluid in the vacuum chamber in response to exposing the portion of the sample fluid to the X-ray beam. The structure of the molecule is then deduced based on the measured scattering, using any method known in the art.

For $10^9$ crystals per milliliter and a nanoflow rate of 0.3 microliters per minute, 5000 crystals pass the focus every second or 250 per sample period, providing enough targets to reliably interact with one femtosecond pulse during the sample period. For example, about ten to fifteen thousand samples of X-ray scattering are obtained per milliliter of sample. This is sufficient to provide statistically significant deduction of target molecule structure from randomly oriented target molecules, or crystals thereof. Due to the statistical nature of this random sampling, it is advantageous to have minimum sample flow required to replenish the sample between each X-ray pulse in order to preserve rare samples.

Tables 2A through 2E indicate X-ray source operation in various embodiments compared to other SFX operations.

TABLE 2A

X-ray operating parameters.

| Sample | Flow rate (ul/min) | Micro-jet diameter (micron) | Total sample consumed (microliter) | Crystal diffraction patterns collected | Crystal patterns/uL |
|---|---|---|---|---|---|
| PSI | 10 | 4 | 5139 | 112725 | 21.9 |
| Lysozyme | 12 to 16 | | | | |
| Lysozyme 40 fs | 10 | 4 | 850 | 16331 | 19.2 |
| 100 fs | 10 | 4 | 230 | 6318 | 27.5 |

TABLE 2A-continued

X-ray operating parameters.

| Sample | Flow rate (ul/min) | Micro-jet diameter (micron) | Total sample consumed (microliter) | Crystal diffraction patterns collected | Crystal patterns/uL |
|---|---|---|---|---|---|
| 150 fs | 10 | 4 | 381 | 4704 | 12.3 |
| 200 fs | 10 | 4 | 375 | 2639 | 7.0 |
| 250 fs | 10 | 4 | 319 | 1681 | 5.3 |
| 300 fs | 10 | 4 | 322 | 2389 | 7.4 |
| Cathepsin B | 15 | 4 | 347 | 988 | 2.8 |
| Reaction center | 10 | 4 | 1000 | 1542 | 1.5 |
| PSI-Fer, gs | 10 | 4 | 1102 | 9086 | 8.2 |
| 5 us | 10 | 4 | 611 | 6839 | 11.2 |
| 10 μs | 10 | 4 | 451 | 3297 | 7.3 |
| PSII | 3~4 | 4 | 855 | 113632 | 132.9 |
| Thermolysin 50 μm ID | 0.3 | 1 | 18 | 14043 | 780.2 |
| Thermolysin 75 μm ID | 1~4 | | 74 | 1064 | 14.4 |
| Lysozyme, 40 fs | 10 | 4 | 2043 | 66442 | 18.4 |
| Lysozyme, 5 fs | 10 | 4 | 2774 | 40115 | 26.3 |

TABLE 2B

X-ray operating parameters (continued).

| Sample | Protein concentration (mg/ml) | Protein consumed (mg) | Crystal patterns/mg | Protein concentration (M) | Crystals/ml |
|---|---|---|---|---|---|
| PSI | 1 | 5.139 | 21935 | 1.00E−06 | 1.00E+09 |
| Lysozyme | | | | | 3.00E+10 |
| Lysozyme 40 fs | 1 | 0.85 | 19213 | 1.00E−06 | |
| 100 fs | 1 | 0.23 | 27470 | 1.00E−06 | |
| 150 fs | 1 | 0.381 | 12346 | 1.00E−06 | |
| 200 fs | 1 | 0.375 | 7037 | 1.00E−06 | |
| 250 fs | 1 | 0.319 | 5270 | 1.00E−06 | |
| 300 fs | 1 | 0.322 | 7419 | 1.00E−06 | |
| Cathepsin B | 2 | 0.694 | 1424 | | 1.00E+09 |
| Reaction center | 5 | 5 | 308 | | |
| PSI-Fer, gs | | | | 3.50E−05 | |
| 5 us | | | | 3.50E−05 | |
| 10 us | | | | 3.50E−05 | |
| PSII | 10 | 8.55 | 13290 | | 5.00E+07 |
| Thermolysin 50 um ID | 14 | 0.252 | 55726 | | 2.00E+10 |
| Thermolysin 75 um ID | 14 | 1.036 | 1027 | | 2.00E+10 |
| Lysozyme, 40 fs | | | | | |
| Lysozyme, 5 fs | | | | | |

TABLE 2C

X-ray operating parameters (continued).

| Sample | Resolution achieved (A) | X-ray energy (keV) | Wavelength (A) | Pulse energy (mJ) | Photons per pulse |
|---|---|---|---|---|---|
| PSI | 8.5 | 1.8 | 6.9 | | 1.00E+12 |
| Lysozyme | 10 | 2 | 6.2 | | >1E+12 |
| Lysozyme 40 fs | | 2 | 6.2 | 0.56 | 1.80E+12 |
| 100 fs | | 2 | 6.2 | 0.56 | 1.80E+12 |
| 150 fs | | 2 | 6.2 | 0.39 | 1.20E+12 |
| 200 fs | | 2 | 6.2 | 0.44 | 1.40E+12 |
| 250 fs | | 2 | 6.2 | 0.41 | 1.30E+12 |
| 300 fs | | 2 | 6.2 | 0.21 | 6.50E+11 |
| Cathepsin B | 8.5 | 1.9954 | 6.2 | 2.13 | 6.70E+12 |
| Reaction center | | 2 | 6.17 | | <10E+13 |
| PSI-Fer, gs | | 2 | 6.9 | 3 | |

TABLE 2C-continued

X-ray operating parameters (continued).

| Sample | Resolution achieved (A) | X-ray energy (keV) | Wavelength (A) | Pulse energy (mJ) | Photons per pulse |
|---|---|---|---|---|---|
| 5 us | | 2 | 6.9 | 3 | |
| 10 us | | 2 | 6.9 | 3 | |
| PSII | 6.5 | 9 | | | 5.00E+11 |
| Thermolysin 50 um ID | | 9.73 | 1.27 | | |
| Thermolysin 75 um ID | | 9.73 | 1.27 | | |
| Lysozyme, 40 fs | 1.9 | 9.4 | 1.32 | 0.6 | 4.00E+11 |
| Lysozyme, 5 fs | 1.9 | 9.4 | 1.32 | 0.053 | 3.50E+10 |

TABLE 2D

X-ray operating parameters (continued).

| Sample | Pulse duration (fs) | X-ray fluence (J/cm$^2$) | X-ray focus (um, FWHM) | Average PULSE irradiance (W/cm$^2$) | X-ray pulses used |
|---|---|---|---|---|---|
| PSI | 10, 70, 200 | 900 | 7 | 1.00E+16 | 1.85E+06 |
| lysozyme | 70-400 | 1200-5300 | 10 | 4E+15 to 7.57E+16 | |
| Lysozyme 40 fs | 70 | | 10 | 1.40E+17 | 306000 |
| 100 fs | 100 | | 10 | 5.60E+16 | 82800 |
| 150 fs | 150 | | 10 | 2.80E+16 | 137000 |
| 200 fs | 200 | | 10 | 2.20E+16 | 135000 |
| 250 fs | 250 | | 10 | 1.60E+16 | 115000 |
| 300 fs | 300 | | 10 | 7.00E+15 | 116000 |
| Cathepsin B | 67.4 | | 2.5 × 3 um | 5.00E+17 | 83224 |
| Reaction center | 70 | | 10 | | 365035 |
| PSI-Fer, gs | 70 | | 7 | 1.00E+17 | 396780 |
| 5 us | 70 | | 7 | 1.00E+17 | 219960 |
| 10 us | 70 | | 7 | 1.00E+17 | 162420 |
| PSII | 50 | | 1.5 | | |
| Thermolysin 50 um ID | 50 | | 1.5 | | |
| Thermolysin 75 um ID | 50 | | 1.5 | | |
| Lysozyme, 40 fs | 40 | | 10 | | 1.47E+06 |
| Lysozyme, 5 fs | 5 | | 10 | | 1997712 |

TABLE 2E

X-ray operating parameters (continued).

| Sample | LCLS pulse rep rate (Hz) | Spots | Reflections | Reference |
|---|---|---|---|---|
| PSI | 6.00E+01 | 2.42E+06 | 3.38E+03 | Chapman et al., Nature, 2011 |
| lysozyme | 60 | | | Lomb et al., Phys Rev. B, 2011 |
| Lysozyme 40 fs | 60 | | | Barty et al., Nature Photonics, 2011 |
| 100 fs | 60 | | | Barty et al., Nature Photonics, 2011 |
| 150 fs | 60 | | | Barty et al., Nature Photonics, 2011 |
| 200 fs | 60 | | | Barty et al., Nature Photonics, 2011 |
| 250 fs | 60 | | | Barty et al., Nature Photonics, 2011 |
| 300 fs | 60 | | | Barty et al., Nature Photonics, 2011 |
| Cathepsin B | 60 | | 514 | Koopman et al., Nature Methods, 2012 |
| Reaction center | 60 | | 2247 | Johannson et al., Nature Methods, 2012 |
| PSI-Fer, gs | 60 | | | Aquila et al., Optics Express, 2012 |
| 5 us | 60 | | | Aquila et al., Optics Express, 2012 |
| 10 us | 60 | | | Aquila et al., Optics Express, 2012 |
| PSII | 120 | | | Kern, PNAS, 2012 |
| Thermolysin 50 um ID | 120 | | | Sierra, Laksmono, et al. 2012 |

TABLE 2E-continued

X-ray operating parameters (continued).

| Sample | LCLS pulse rep rate (Hz) | Spots | Reflections | Reference |
|---|---|---|---|---|
| Thermolysin 75 um ID | 120 | | | Sierra, Laksmono, et al. 2012 |
| Lysozyme, 40 fs | 120 | | 9921 | Boutet, Science, 2012 |
| Lysozyme, 5 fs | 120 | | 9743 | Boutet, Science, 2012 |

Figure 5A:
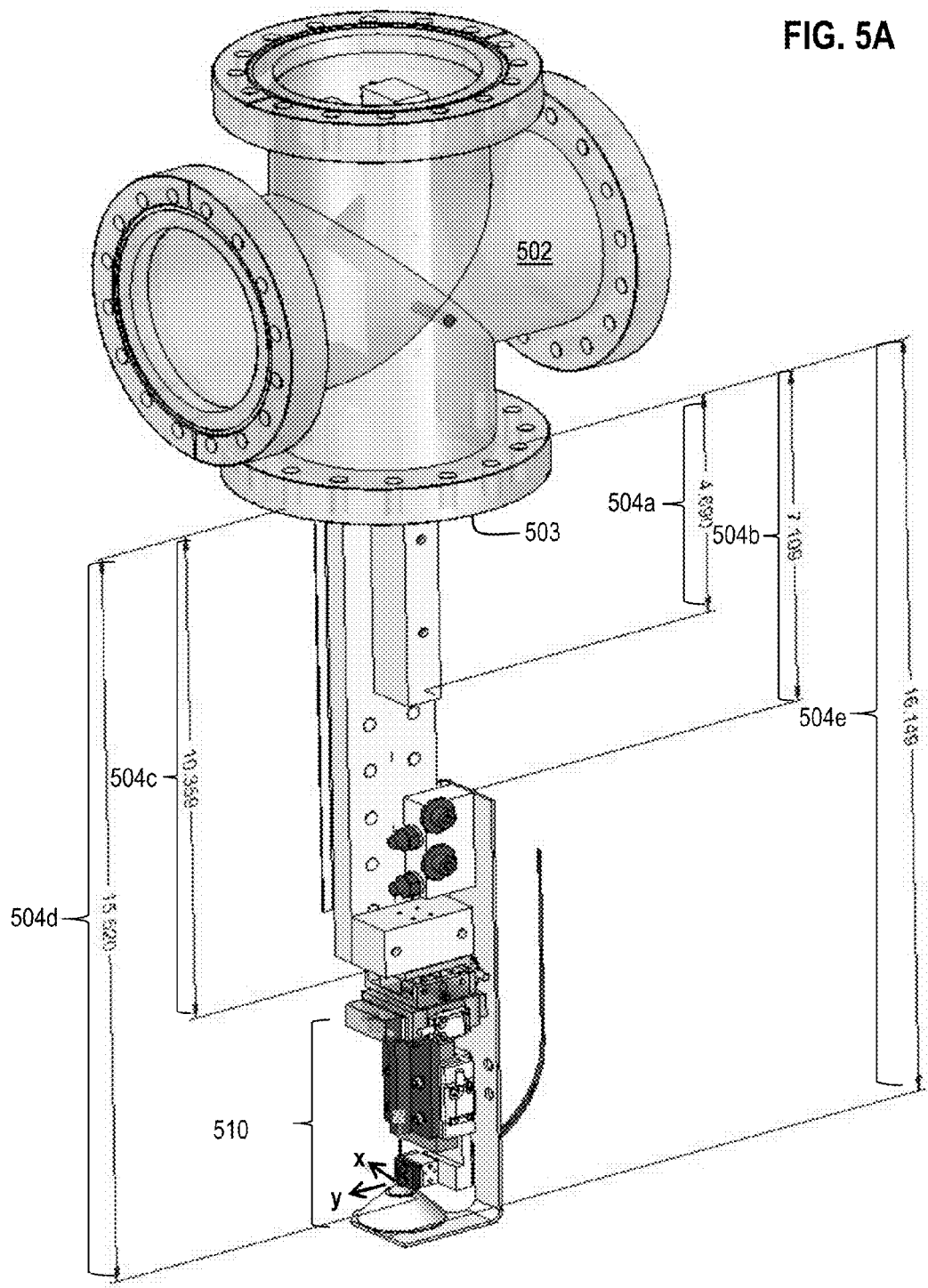
FIG. 5A and FIG. 5B are block diagrams that illustrate spacing of components of the FIG. 1 apparatus for the Linac Coherent Light Source's (LCLS) Coherent X-ray Imaging (CXI) endstation, according to an embodiment.
Figure 5B:
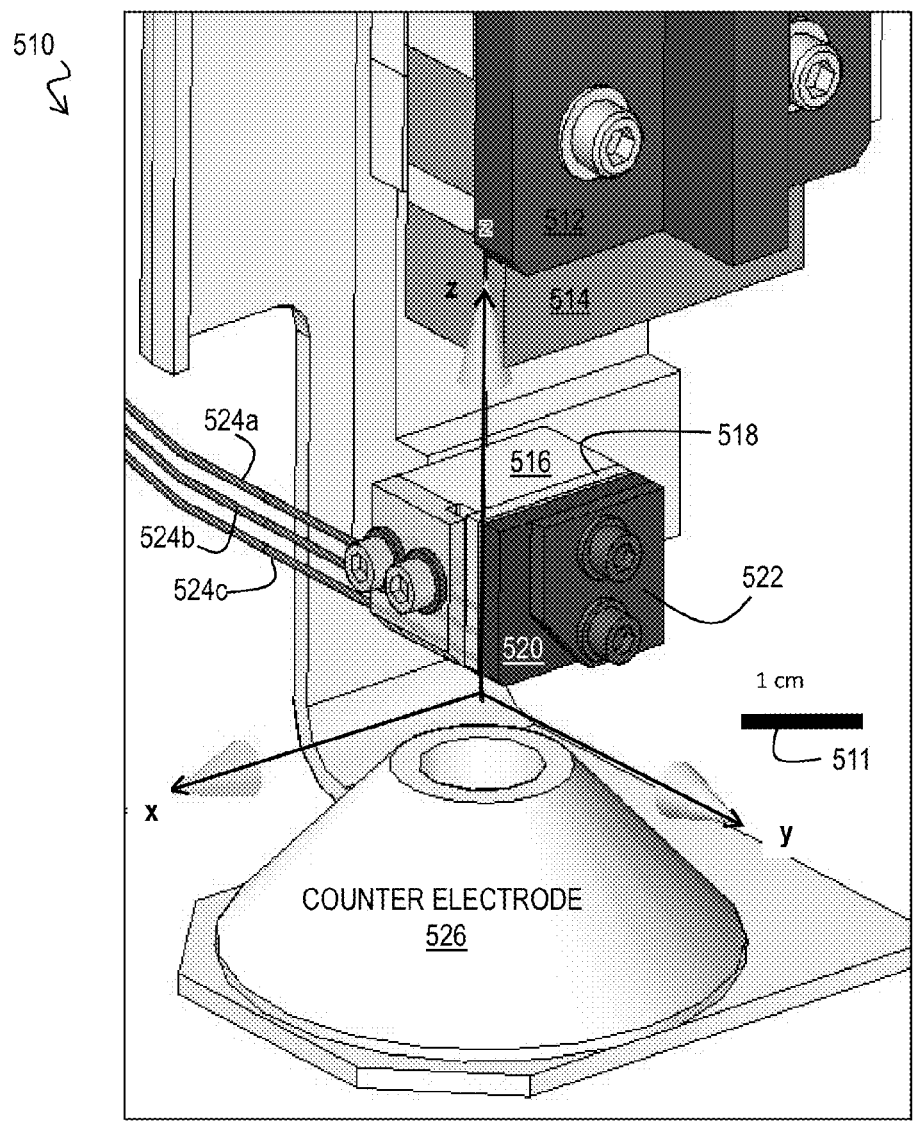

FIG. 5A and FIG. 5B are block diagrams that illustrate spacing of components of the FIG. 2 apparatus for the Linac Coherent Light Source's (LCLS) Coherent X-ray Imaging (CXI) endstation, according to an embodiment. The CAD drawing of FIG. 5A depicts the spacing of various components between a vacuum chamber fitting 502 and the electrospray components 510. The distance 504a is 4.690 inches from a breadboard mount to the conflat flange 503 of vacuum chamber fitting 502. The distance 504b is 7.109 inches from a counter electrode mount to the conflat flange 503 of vacuum chamber fitting 502. The distance 504c is 10.359 inches from an XYZ nanopositioning motor mount to the conflat flange 503 of vacuum chamber fitting 502. The distance 504d is 15.520 inches from the top of a counter electrode 246 to the conflat flange 503 of fitting 502. The distance 504e is 16.149 inches from the bottom of a counter electrode 246 mount to the conflat flange 503 of vacuum chamber fitting 502. The X direction denotes the x-ray beam path.

FIG. 5B is a diagram that depicts the electrospray components 510 and components useful for optical illumination of sample within the silica capillary 236 prior to formation of the jet, according to an embodiment. Spacing is indicated by scale bar 511 representing 1 centimeter (cm, 1 cm=$10^{-2}$ meters). This includes nanoscale stepping motor 512 and its mount 514. Other components include a base mount 516, a compression mount 518 for the silica capillary 236, a laser dump 520 to capture light emitted from optical fibers 524a, 524b, 524c, a compression clamp 522 to hold together the assembly of 236, 518 and 520 and counter electrode 526.

Figure 6:
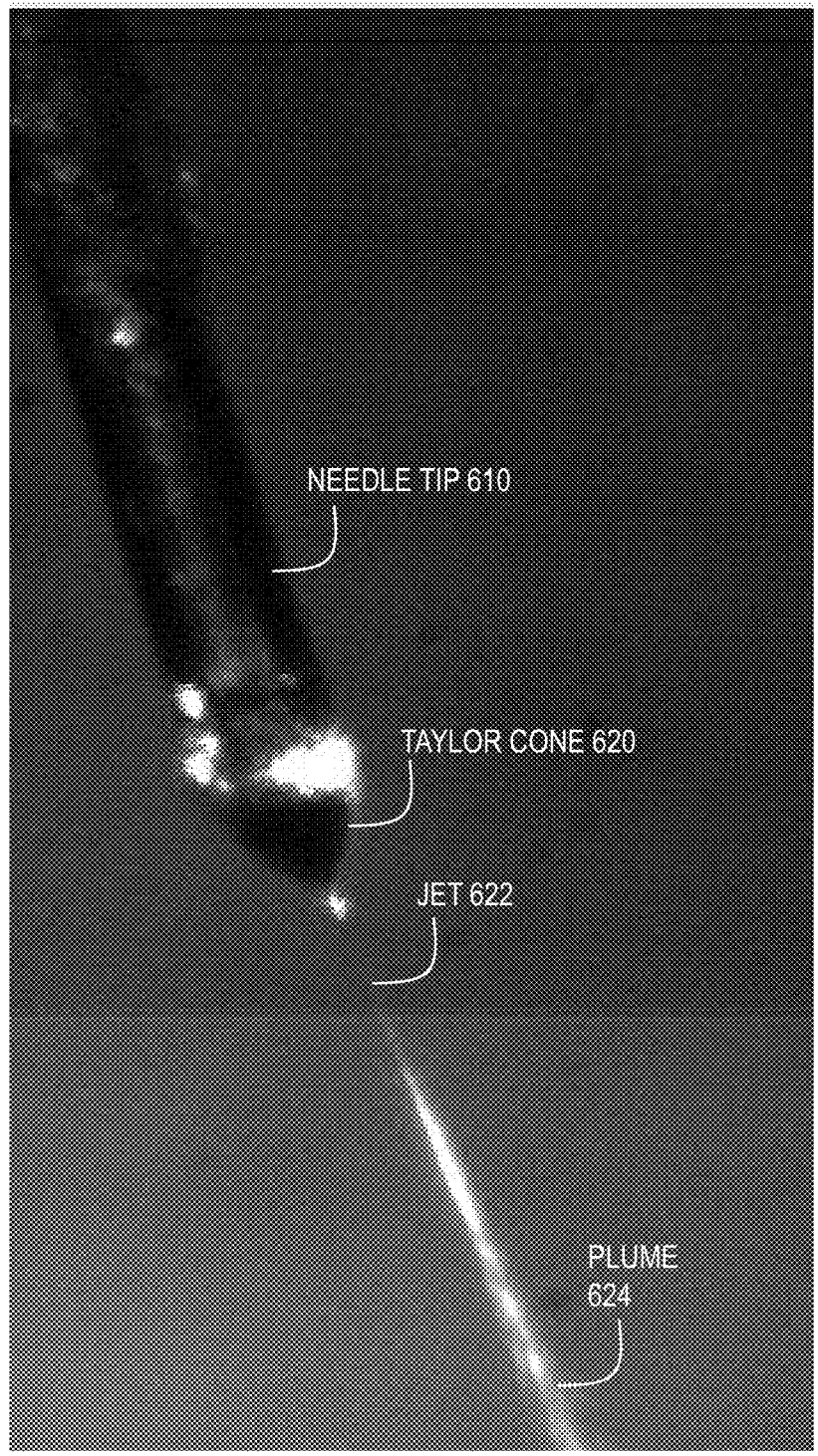
FIG. 6 is a is a photograph that illustrates example electrospray produced by apparatus of FIG. 5A and FIG. 5B, according to an embodiment.

FIG. 6 is a photograph that illustrates example electrospray produced by apparatus of FIG. 5A and FIG. 5B, according to an embodiment. The tapered needle tip 610 exudes a Taylor cone 620, nanoflow liquid jet 622 and start of plume 624. FIG. 6 depicts a tapered fused silica capillary (74 μm×150 μm) needle tip 610 inside the CXI chamber, back-illuminated by a red LED and a laser (flowing the carrier solution described above), with a pressure of $3\times10^{-3}$ torr, inside the CXI chamber. Typical chamber pressure and liquid flow rate nominally $\sim 10^{-5}$ torr and 0.4 μL/min.

The relative performance of the nanoflow electrospinning and the GDVN are compared in Table 3 for one embodiment.

TABLE 3

Electrospinning in vacuo comparison with GDVN

| Parameters | Gas Dynamic Virtual Nozzle (Arizona State U.) | Electrospun Nanofiber in vacuo (PULSE) |
|---|---|---|
| Flow focusing phenomenon | Gas | Electrokinetic |
| Capillary Diameter | 40-50 μm | 50, 75, 100, 150 μm |
| Gas Sheath | Helium >300 psi | none |
| Liquid backing pressure | >200 psi | 15-20 psi |
| Sample consumption | 5-40 μl/min | 0.14-10 μl/min |
| Jet diameter | 1-20 μm | 1-10 μm |
| Observed hit rates at CXI | ~2% | ~2% (non-identical samples), to 25% |
| Sample solvent | Water, lipidic cubic phase | 30% glycerol/10% PEG 2000 |
| Sample delivery | Rotating syringe mount/loop | Microcentrifuge tube |
| Sample volume (30 min) | 300 μl | 9, 90, 270 μl (50/75/100 μm ID capillary) |
| Operating pressure for SFX | $10^{-3}$ Torr, $10^{-6}$ Torr with metal sheath surrounding apparatus | $7 \times 10^{-5}$ Torr, no metal shroud |

The electrostatic liquid jet illustrated in FIG. 6 is used to perform SFX with 20 times lower sample consumption rate, e.g., a flow rate of 500 nanoliters per minute. Experiments with both a 50 micron inner diameter capillary and a 75 micron inner diameter capillary are given in Table 4. This experiment consumed 0.046 ml of sample fluid and produced an average of 3 hits per second. Using GDVN, to index three times as many hits consumed 2.6 ml—not three times the volume, but 56 times the volume consumed by the nanoflow liquid jet in vacuo.

TABLE 4

Serial Femtosecond X-ray crystallography experimental statistics

| Inner diameter (microns) | Time (minutes) | Total shots | Total hits | Total indexed | % of hits indexed | % of shots indexed |
|---|---|---|---|---|---|---|
| 50 | 68 | 489614 | 14043 | 4234 | 30 | 0.86 |
| 75 | 24.68 | 177671 | 1064 | 331 | 31 | 0.19 |
| all | 92.68 | 667285 | 15107 | 4565 | 30.5 | 0.68 |

Figure 7:
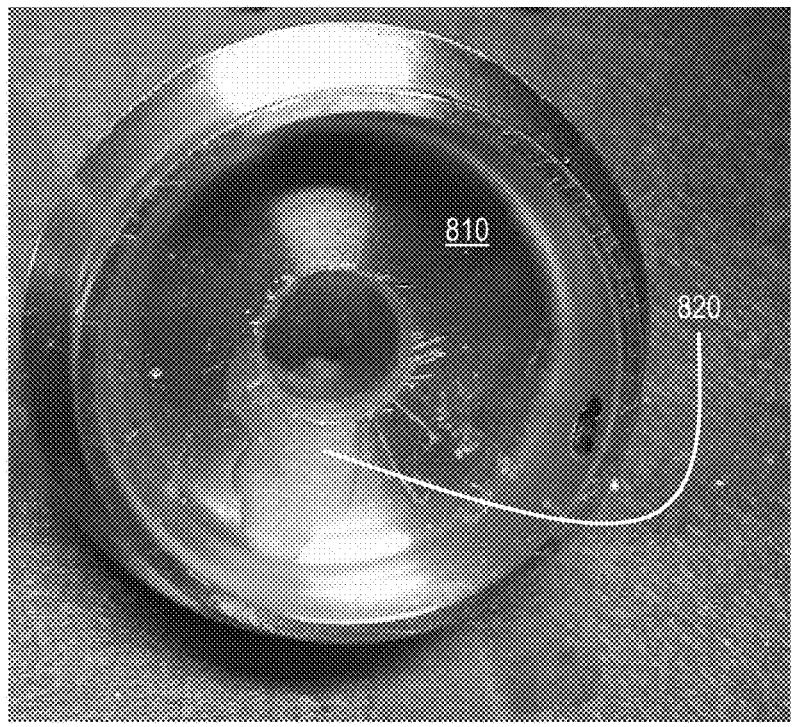
FIG. 7 and FIG. 8 are photographs that illustrate example reduction of sample fluid collection on counter-electrode, according to an embodiment.
Figure 8:
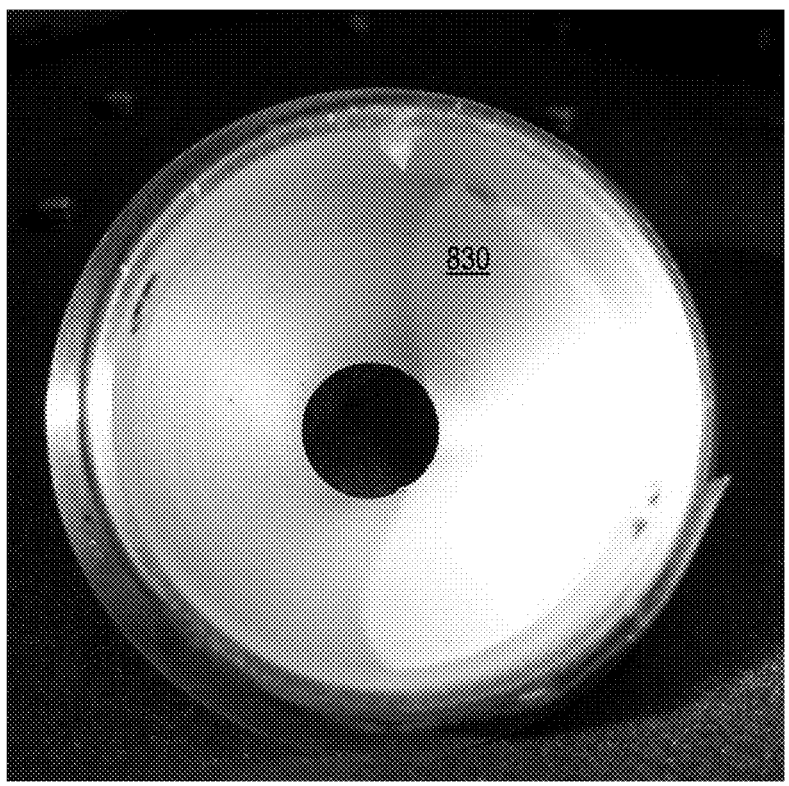

In another embodiment, a new counter electrode was designed and built, and operated with a centered capillary. Long term (48 hour) testing of new design was performed with 30/10 glycerol/PEG 2000. Repeated 1.5 ml sample fluid, 24 hr tests were performed. New buffer conditions with Sucrose/PEG 2000 were explored. FIG. 7 and FIG. 8 are photographs that illustrate example reduction of sample fluid 820 collection on counter-electrodes 810 and 830, according to an embodiment. It is concluded that new counter electrode design runs continuously for days with no sample buildup when capillary centered (75 um ID capillary, 1 µl/min flow rate). This is a huge improvement because, previously, intervention due to sample fluid collection 820 reaching the x-ray interaction region was required at 4 hrs. It was further concluded that: though multiple capillaries can be used, a single capillary will produce most reproducible jetting conditions; sucrose can substitute glycerol, and, in some embodiments, a Kapton heater is attached to the counter electrode to reduce sample fluid collection 820.

In some experiments, injection of the samples into the interaction region was achieved by focusing the crystal suspension exiting a silica capillary (100 µm inner diameter) into a jet smaller than 10 µm in diameter using an electric potential of 2.1-2.5 keV between the capillary exit and a counter electrode 7 mm away. The crystal suspension flowed at 2.5-3.1 µl/min using a liquid backing pressure of 15-20 psi. Buffer B with 10% PEG 2000 does not electrospray in vacuum due to freezing at the nozzle exit. Glycerol was added as a cryoprotectant to eliminate freezing and enable formation of a stable cone-jet mode. Surprisingly, the combination of glycerol and PEG 2000 in the buffer also contributed to the low flow rate operation and reduced settling of the crystals during the experiment. The X-rays probed the liquid jet 50-100 µm from the exit of the capillary, exposing the crystal suspension to vacuum for fractions of a second.

In another embodiment, the X-ray diffraction pattern of PS II isolated from the thermophilic cyanobacterium Thermosynechococcus elongatus, was collected at the Coherent X-ray Imaging (CXI) instrument at LCLS using the single-shot approach. PS II microcrystals (~10 µm) were injected into the LCLS X-ray beam in a liquid jet based on the electrohydrodynamic spraying of glycerol in vacuum using cone-jet mode. Several thousand diffraction images were collected at random crystal orientations. A single-shot diffraction pattern from a microcrystal exhibits Bragg spots up to 5.4 Å resolution. The Bragg spots are remarkably sharp and small, spreading over only a few pixels. This is likely due to the combination of low crystal mosaicity and the use of pixel-array detector technology with an extremely narrow point-spread function. The diffraction intensities varied strongly from shot to shot due to several factors, such as the size of the probed crystal volume, the quality of the microcrystals and orientation, and variations in the intensity of the beam due to the nature of the LCLS X-ray pulses.

Figure 9:
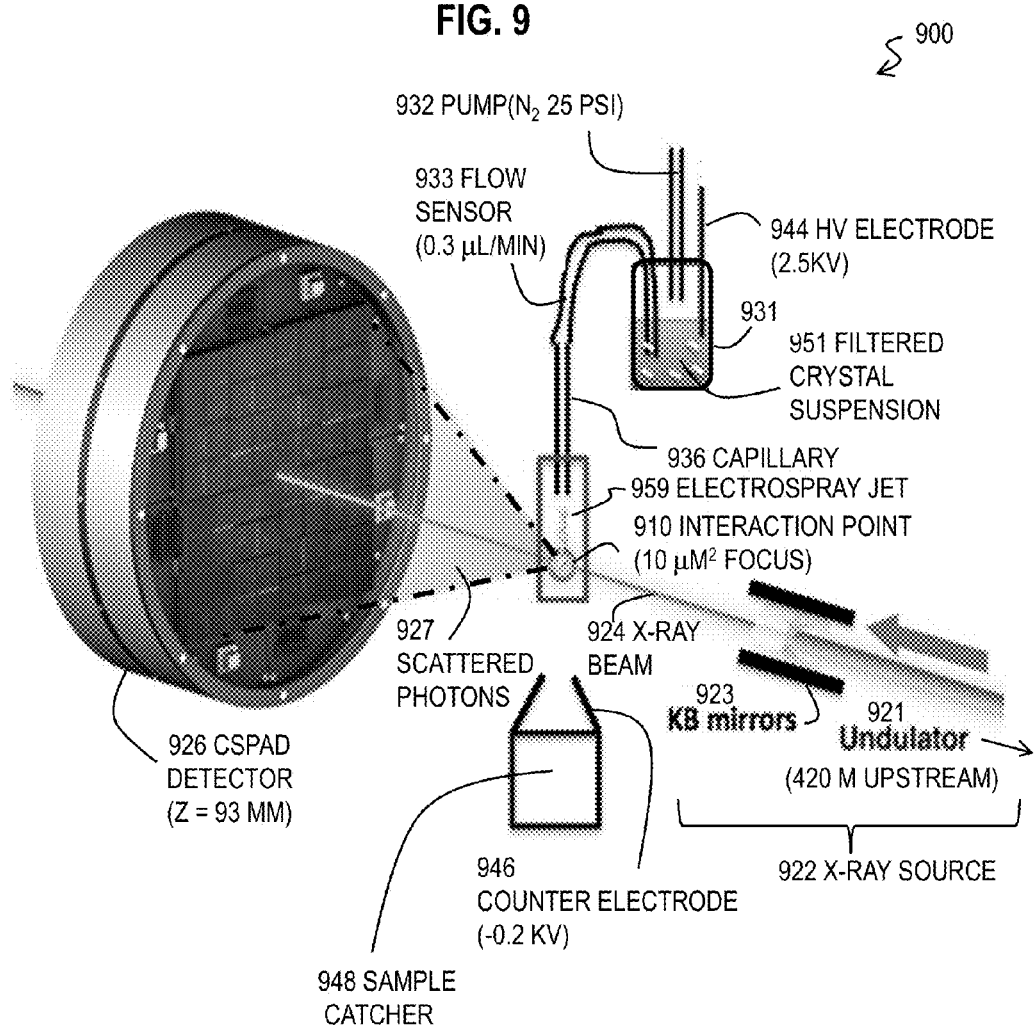
FIG. 9 is a block diagram that illustrates an experimental nanoflow liquid jet for SFX, according to an embodiment.

Experiments were carried out at the CXI instrument at LCLS. FIG. 9 is a block diagram 900 that illustrates an experimental nanoflow liquid jet for SFX, according to an embodiment. This was the experimental setup for a SFX experiment at the LCLS CXI endstation. The endstation includes an interaction point 910 with a 10 square micron focus resulting from KB mirrors 923 focusing X-ray synchrotron radiation output by an undulator 921 located 420 meters upstream of the interaction point 910. The KB mirrors 923 and undulator 921 collectively form an X-ray source 922. The Bragg scattered photons 927 from a target at the interaction point 910 is captured at a CSPAD detector 926 located 93 millimeters (mm, 1 mm=$10^{-3}$ meters) downstream from the interaction point 910.

A crystal suspension was prepared of 1-2 micron thermolysin crystals in 30% v/v glycerol, with 10% polyethylene glycol (PEG) 2000, $CaCl_2$, dissolved in deionized water. The crystals were then filtered through an 8 µm pore size Nucleopore membrane (Whatman). A 100 µL aliquot of the sample (filtered crystal suspension 951) in a microcentrifuge tube was loaded into the pressurized cell 931 of a TSI electrospray aerosol generator (3980) from TSI Inc. of Shoreview, Minn. A solution high voltage (HV) electrode 944 was immersed in the sample 951. A 114 cm long, 50 µm ID capillary 936 delivered the sample crystal suspension 951 to the interaction region inside the vacuum chamber through a ¹⁄₁₆" Swagelok fitting. The capillary 936 was fixed to an XYZ nanopositioning stage (PI Micos PP-30 from PI USA of Auburn, Mass.) to enable positioning relative to the focused X-ray beam.

A counter electrode 946 was 1 cm in diameter and positioned 5 to 7 mm from the capillary exit. A sample catcher 948 backed up the counter electrode 946. The nanoflow liquid jet 959 was visualized using a CXI microscope on-axis with the X-rays and was facilitated with illumination by a nanosecond pulsed laser (532 nm wavelength).

During operation, 2.5 kiloVolts (kV, 1 kV=$10^3$ volts) was applied to the solution high voltage (HV) electrode 944 and −0.2 kV was applied to the counter electrode 946. An nanoflow liquid jet 959 flowing at 0.3 µl/min at flow sensor 933 was emitted from the 50 micron ID silica capillary 936 positioned less than about 1 mm from the XFEL interaction region surrounding interaction point 910. Single pulse diffraction patterns from single crystals flowing in the nanoflow liquid jet were recorded on the CSPAD detector 926 at a 120 Hz repetition rate of the LCLS. Each 40 femtosecond pulse delivered an average of 3 milliJoules (mJ, 1 mJ=$10^{-3}$ Joules) focused at the interaction point 910 using 9.7 keV X-rays in beam 924. Thus FIG. 9 depicts nanoflow liquid jet serial femtosecond crystallography at the Coherent X-ray Imaging endstation for protein nanocrystals in vacuo.

Figure 10A:
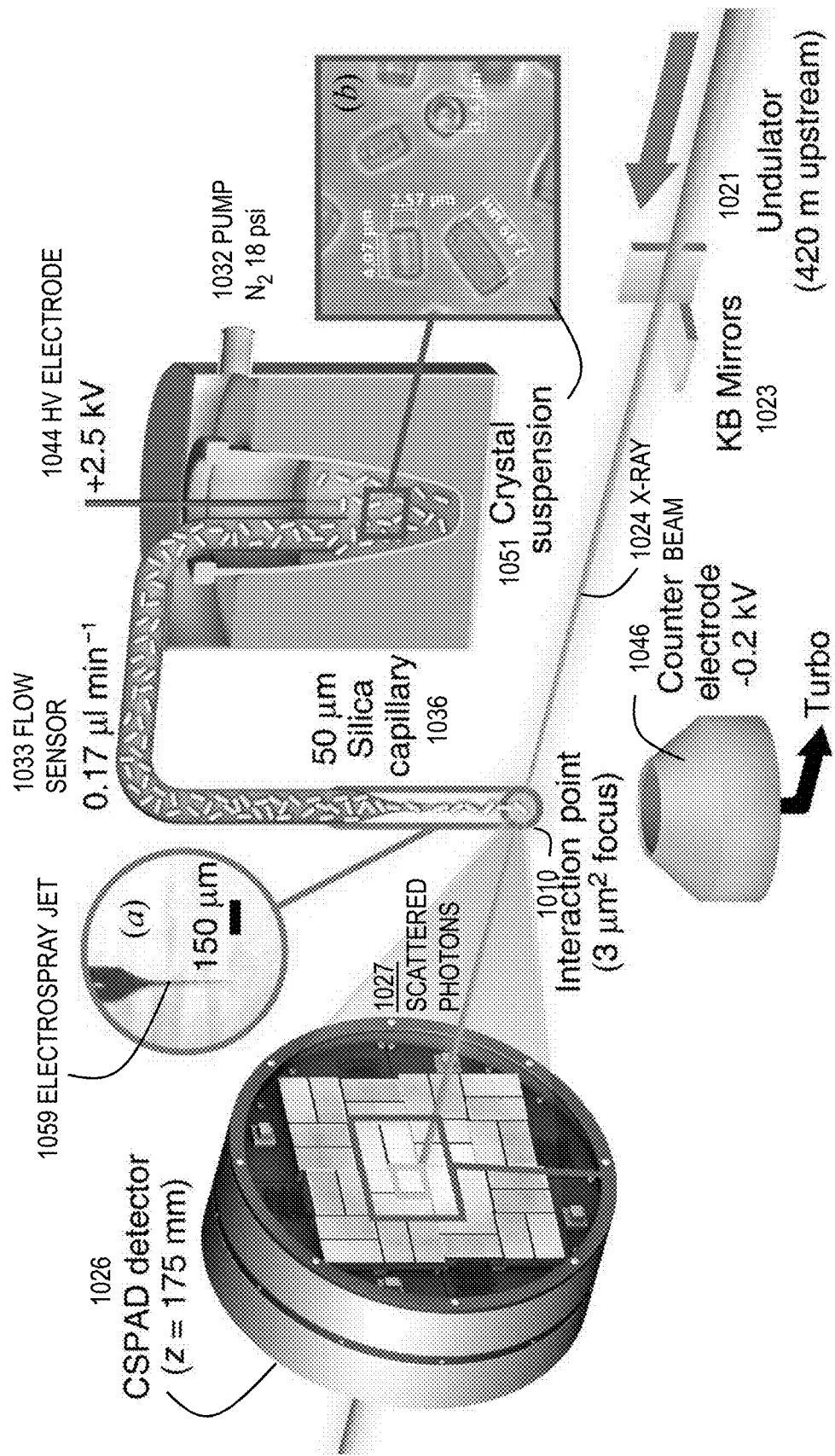
FIG. 10A is a block diagram that illustrates an experimental nanoflow liquid jet for SFX, according to another embodiment

FIG. 10A is a block diagram that illustrates an experimental nanoflow liquid jet for SFX, according to another embodiment. The endstation includes an interaction point 1010 with a 3 square micron focus resulting from KB mirrors 1023 focusing X-ray synchrotron radiation output by an undulator 1021 located 420 meters upstream of the interaction point 1010. The Bragg scattered photons 1027 from a target at the interaction point 1010 is captured at a CSPAD detector 1026 located 175 mm downstream from the interaction point 1010.

A crystal suspension 1051 was prepared. A solution high voltage (HV) electrode 1044 was immersed in the sample 1051. A 114 cm long, 50 µm ID capillary 1036 delivered the sample crystal suspension 1051 to the interaction region inside the vacuum chamber.

During operation, 2.5 kV was applied to the solution high voltage (HV) electrode 1044 and −0.2 kV was applied to the counter electrode 1046. An nanoflow liquid jet 1059 flowing at 0.17 µl/min at flow sensor 1033 was emitted from the 50 micron ID silica capillary 1036 to interaction point 1010. Single pulse diffraction patterns from single crystals flowing in the nanoflow liquid jet were recorded on the CSPAD detector from X-rays in beam 1024.

Figure 10B:
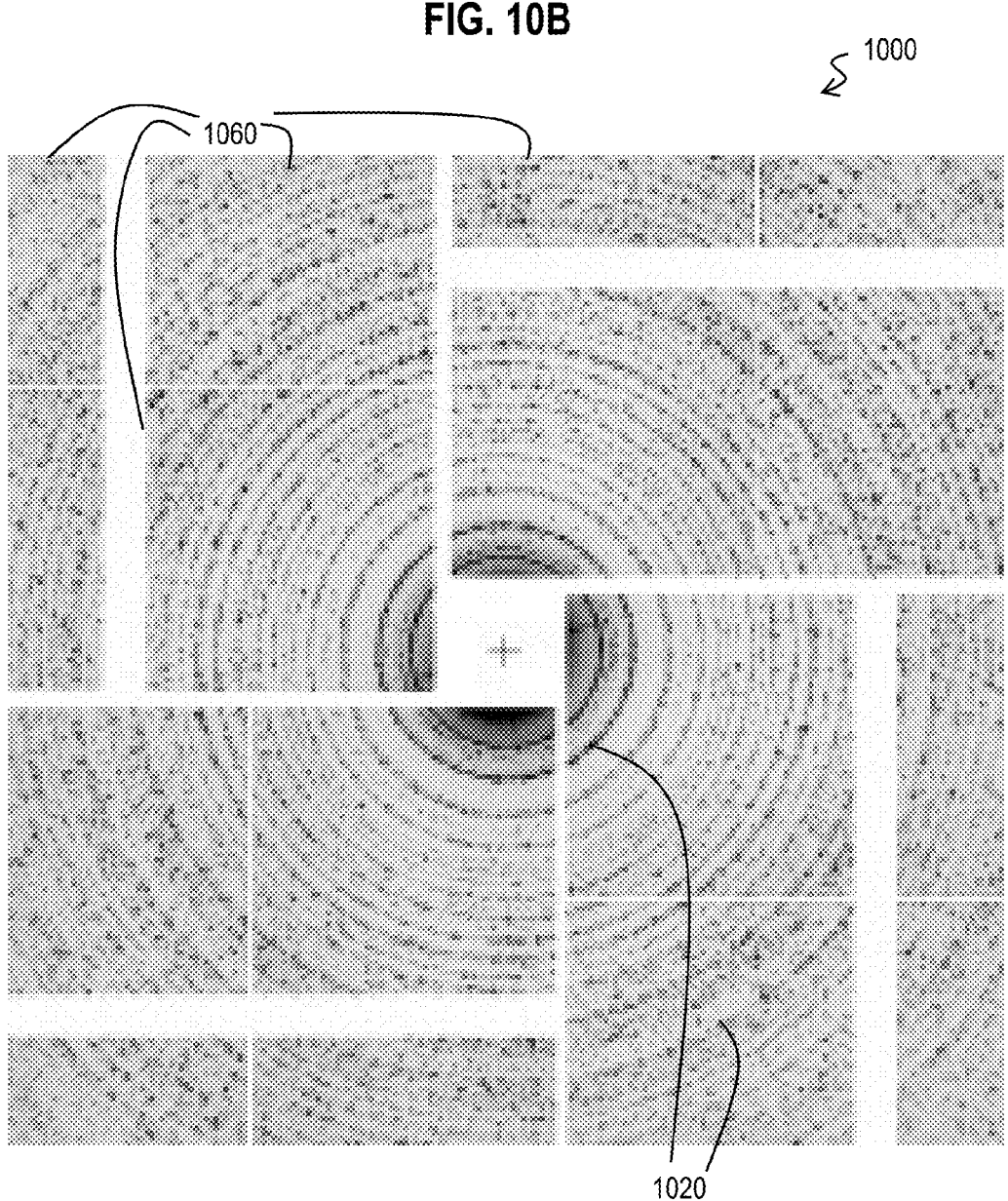
FIG. 10B is a block diagram that illustrates panels of pixels that record X-ray scattering intensity from crystals in a nanoflow liquid jet of FIG. 10A, according to an embodiment.

FIG. 10B is a block diagram 1000 that illustrates panels 1060 of pixels that record X-ray scattering intensity 1020 from crystals in a nanoflow liquid jet of FIG. 10A, according to an embodiment. Thus FIG. 10B depicts serial femtosecond crystallography of electrospun thermolysin crystals in a nanoflow liquid jet. The image exhibits a sum of about 10,000 single-shot FEL diffraction patterns from 1-2 micron thermolysin crystals in different orientations. At the edge of the detector, a maximum resolution of 1.5 Å was achieved.

In other experimental embodiments, the CXI instrument at LCLS was operated at an energy of 9 keV with an average intensity of $3\text{-}5\times10^{11}$ photons/pulse, a pulse frequency of 120 Hz and a pulse duration of <50 fs. The beam was focused to a size of about 1.5 µm full width at half maximum (FWHM) at the interaction region. Forward diffraction was measured using the CSPAD detector of the CXI instrument with a pixel size of $110\times110$ µm² and a total of 2.3 million pixels. The detector metrology was established using Ag behenate, microcrystals of thermolysin, and LCLS-provided optical data. Flux numbers were converted into deposited energy (dose) using the program RADDOSE.

PS II diffraction data was processed with a new software suite (cctbx.xfel from Lawrence Berkeley National Laboratory, Berkeley, Calif.) that builds upon components developed previously in the synchrotron context for picking Bragg spots (spotfinder Lawrence Berkeley National Laboratory, Berkeley, Calif.) and autoindexing (labelit Lawrence Berkeley National Laboratory, Berkeley, Calif.), and employs established methods for the integration of Bragg spot intensities by pixel summation. Individual reflections were scaled and merged without separately accounting for the partiality fraction of each observation. The structure was solved by molecular replacement using Phaser from University of Cambridge, Cambridge, United Kingdom.

In some embodiments, the injector is comprised of many off-the-shelf parts. The capillary is a tapered 1 m long borosilicate glass capillary, New Objective, Woburn, Mass., with inner diameters of 50 µm, 75 µm, and 100 µm. The reservoir used in Siena, Laksmono, et al., 2012, was a tapered Eppendorf, Hamburg, Germany, microcentrifuge tube that was placed inside of a pressure cell from a TSI, Inc., Shoreview, Minn., electrospray box. A more off-the-shelf reservoir has been developed and used in unpublished work. It involves a Shimadzu, Tokyo, Japan, autosampler vial which acts as the reservoir for the crystal suspension. There is a simpler 300 µL polypropylene vial with a PTFE/silicone septum. For better visibility of the sample, a 200 µL "Q-sert" glass autosampler vial is used. Both use plastic caps with a polymer septum which allows the capillary, platinum electrode, and pressure line to pierce through and interact with the fluid in the reservoir. Both the capillary and platinum electrode use Upchurch, Oak Harbor, Wash., polymer sleeves 1/16 inch×0.155 inch and 0.011 inch×0.025 inch, respectively, to easily pass in and out of the septum. The capillary tip and platinum electrode are submerged near the bottom of the reservoir, while ensuring that the sleeve is not submerged below the fluid level. The reservoir is pressurized by a nitrogen gas line that interfaces with a ¼ inch, 20 gage stainless steel blunt tip Luer Lock needle. Pressures of 0-20 psig are typically applied.

Figure 11:
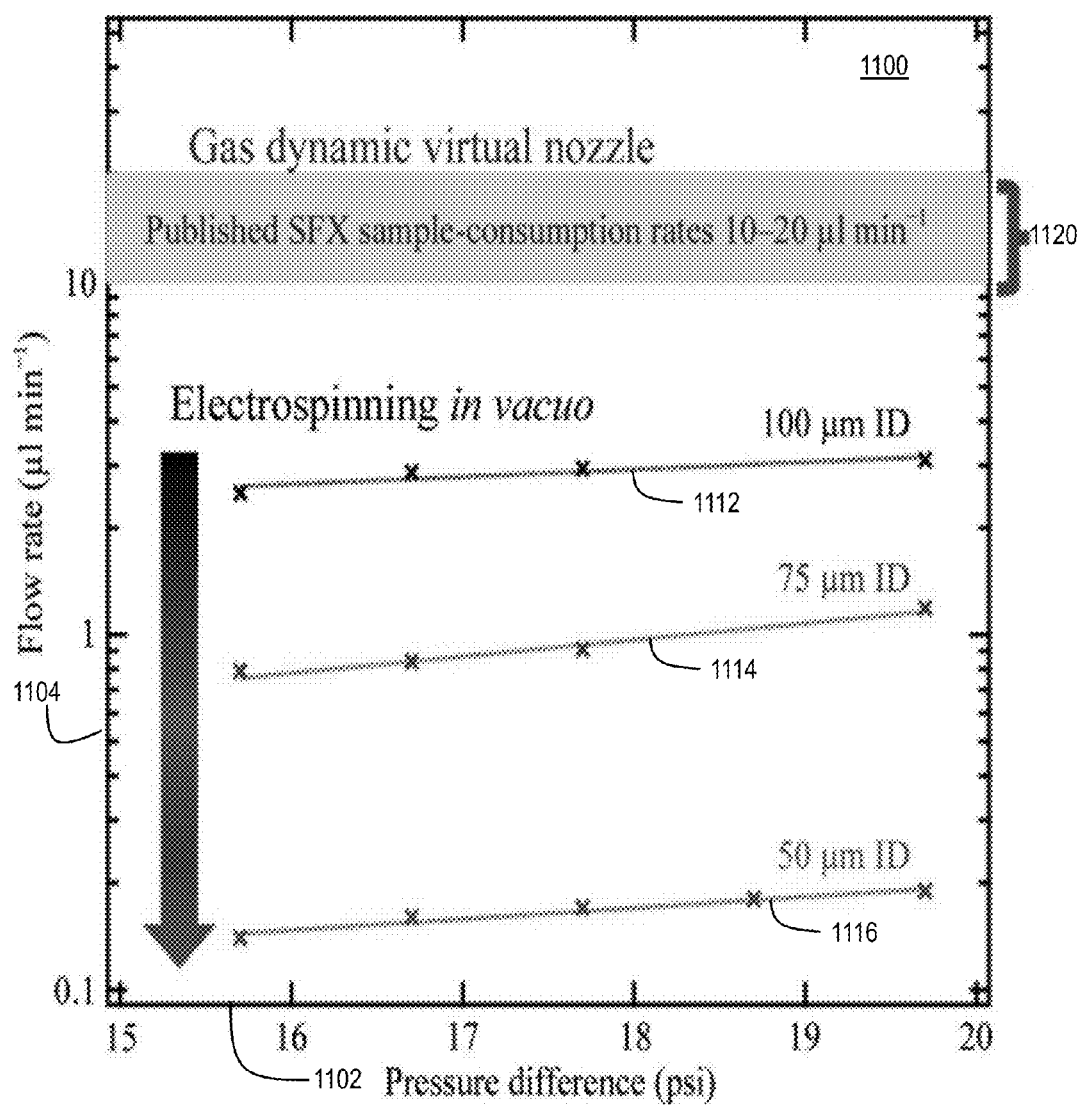
FIG. 11 is a graph that illustrates example flow rate measurement made during example electrospun liquid jets experiments, according to various embodiments.

FIG. 11 is a graph 1100 that illustrates example flow rate measurement made during example electrospun liquid jets experiments using 30% glycerol and 10% PEG 2000 liquid for various capillaries inner diameter (50-100 µm), according to various embodiments. The horizontal axis 1102 indicates pressure difference applied by a the pump 932 or 1032, in psi. The logarithmic vertical axis 1104 indicates flow rate in µl/min. Using a 100 micron inner diameter capillary, points along trace 1112 are obtained, with flow rates between about 2 and about 3 µl/min. Using a 75 micron inner diameter capillary, points along trace 1114 are obtained, with flow rates between about 0.8 and about 1.1 µl/min. Using a 50 micron inner diameter capillary, points along trace 1116 are obtained, with flow rates between about 0.12 and about 0.2 µl/min. Thus flow rates below about 3 µl/min are obtained. In contrast, flow rates from GDVN are much higher as indicated by region 1120, e.g., at about 10 µl/min and above, even using greater pressure differences than on axis 1102.

In embodiments for which results are depicted in FIG. 11, sample flow rate was measured for a sample solution of 30% (by weight or volume, indicates by w/v) glycerol, 10% (w.v) PEG 2000, pH 6.5, 5 mM CaCl2, 100 mM MES buffer solution. The sample solution was emitted into vacuum from capillary tubes of inner diameter (ID) 50 microns, or 75 microns or 100 microns that were 114 cm long or 110 cm long or 120 cm long, respectively.

In some embodiments, carrier fluid comprises 10% by volume PEG 2000 and 30% sucrose solution with a sucrose concentration in a range from about 1.1 Molar to about 1.4 Molar. Table 5 summarizes flow rate for electrospun jet in vacuo with various sucrose concentrations and 10% PEG 2000 liquid through 100 cm long capillary with a 75 micron or 100 micron inner diameter.

TABLE 5

Flow rate for various sucrose concentrations and 10% PEG 2000 liquid in capillaries of different inner diameter (ID).

| Sucrose (Molar) | ID (microns) | ΔP (psi) | Flow Rate (µl/minute) |
|---|---|---|---|
| 1.1 | 75 | 15.7 | 0.73 |
| 1.1 | 75 | 17.7 | 0.75 |
| 1.1 | 75 | 19.7 | 0.79 |
| 1.2 | 75 | 15.7 | 0.58 |
| 1.2 | 75 | 17.7 | 0.62 |
| 1.2 | 75 | 19.7 | 0.66 |
| 1.4 | 75 | 15.7 | 0.33 |
| 1.4 | 75 | 17.7 | 0.40 |
| 1.4 | 75 | 19.7 | 0.53 |
| 1.1 | 100 | 15.7 | 1.84 |
| 1.1 | 100 | 17.7 | 2.15 |
| 1.1 | 100 | 19.7 | 2.43 |
| 1.2 | 100 | 15.7 | 1.5 |
| 1.2 | 100 | 17.7 | 1.7 |
| 1.2 | 100 | 19.7 | 1.81 |
| 1.4 | 100 | 15.7 | 1.15 |
| 1.4 | 100 | 17.7 | 1.2 |
| 1.4 | 100 | 19.7 | 1.41 |

Electrospun liquid jets have several features valuable for SFX experiments: simple design—no differential pumping shroud surrounds the jet and sample is loaded in a microcentrifuge tube, low flow rate (about 0.14 to about 3.1 µl/min), compatibility with highly viscous solutions (i.e. 30% glycerol) often used for biological samples, open silica capillary design enables fiber optical laser integration for future pump-probe experiments. Nanoflow liquid jet with protein crystals in vacuo complements the GDVN approach; and the ability of the nanoflow liquid jet to operate with few hundred nanoliter per minute flow rate opens SFX to a wider array of structural biology problems The techniques presented here enable several applications. In general, the characteristics are: Lower sample consumption rate opens SFX to more precious samples; simple design allows for facile sample recovery; sample settling issue is resolved using highly viscous solutions; open access in the vacuum chamber facilitates complex experiments such as simultaneous x-ray emission spectroscopy/x-ray diffraction or time-resolved pump-probe experiments. National laboratory uses enabled include: SFX with 4th generation x-ray lasers like the LCLS and Next Generation Light Source; SFX at 3rd generation synchrotrons; other single-shot x-ray diffraction experiments such as virus imaging, catalytic nanomaterials, or solution scattering; and, sample delivery source for mass spectrometers. Commercial possibilities include SFX with 4th generation x-ray lasers like the LCLS and Next Generation Light Source; SFX at 3rd generation synchrotrons; other single-shot x-ray diffraction experiments such as virus imaging, catalytic nanomaterials, or solution scattering; and, sample delivery source for mass spectrometers.

Controller Hardware Overview

FIG. 12 is a block diagram that illustrates a computer system 1200 upon which an embodiment of the invention may be implemented. Computer system 1200 includes a communication mechanism such as a bus 1210 for passing information between other internal and external components of the computer system 1200. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1200, or a portion thereof, constitutes a means for performing one or more steps of one or more methods described herein.

A sequence of binary digits constitutes digital data that is used to represent a number or code for a character. A bus 1210 includes many parallel conductors of information so that information is transferred quickly among devices coupled to the bus 1210. One or more processors 1202 for processing information are coupled with the bus 1210. A processor 1202 performs a set of operations on information. The set of operations include bringing information in from the bus 1210 and placing information on the bus 1210. The set of operations also typically include comparing two or more units of information, shifting positions of units of information, and combining two or more units of information, such as by addition or multiplication. A sequence of operations to be executed by the processor 1202 constitutes computer instructions.

Computer system 1200 also includes a memory 1204 coupled to bus 1210. The memory 1204, such as a random access memory (RAM) or other dynamic storage device, stores information including computer instructions. Dynamic memory allows information stored therein to be changed by the computer system 1200. RAM allows a unit of information stored at a location called a memory address to be stored and retrieved independently of information at neighboring addresses. The memory 1204 is also used by the processor 1202 to store temporary values during execution of computer instructions. The computer system 1200 also includes a read only memory (ROM) 1206 or other static storage device coupled to the bus 1210 for storing static information, including instructions, that is not changed by the computer system 1200. Also coupled to bus 1210 is a non-volatile (persistent) storage device 1208, such as a magnetic disk or optical disk, for storing information, including instructions, that persists even when the computer system 1200 is turned off or otherwise loses power.

Information, including instructions, is provided to the bus 1210 for use by the processor from an external input device 1212, such as a keyboard containing alphanumeric keys operated by a human user, or a sensor. A sensor detects conditions in its vicinity and transforms those detections into signals compatible with the signals used to represent information in computer system 1200. Other external devices coupled to bus 1210, used primarily for interacting with humans, include a display device 1214, such as a cathode ray tube (CRT) or a liquid crystal display (LCD), for presenting images, and a pointing device 1216, such as a mouse or a trackball or cursor direction keys, for controlling a position of a small cursor image presented on the display 1214 and issuing commands associated with graphical elements presented on the display 1214.

In the illustrated embodiment, special purpose hardware, such as an application specific integrated circuit (IC) 1220, is coupled to bus 1210. The special purpose hardware is configured to perform operations not performed by processor 1202 quickly enough for special purposes. Examples of application specific ICs include graphics accelerator cards for generating images for display 1214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1200 also includes one or more instances of a communications interface 1270 coupled to bus 1210. Communication interface 1270 provides a two-way communication coupling to a variety of external devices that operate with their own processors, such as printers, scanners and external disks. In general the coupling is with a network link 1278 that is connected to a local network 1280 to which a variety of external devices with their own processors are connected. For example, communication interface 1270 may be a parallel port or a serial port or a universal serial bus (USB) port on a personal computer. In some embodiments, communications interface 1270 is an integrated services digital network (ISDN) card or a digital subscriber line (DSL) card or a telephone modem that provides an information communication connection to a corresponding type of telephone line. In some embodiments, a communication interface 1270 is a cable modem that converts signals on bus 1210 into signals for a communication connection over a coaxial cable or into optical signals for a communication connection over a fiber optic cable. As another example, communications interface 1270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1270 sends and receives electrical, acoustic or electromagnetic signals, including infrared and optical signals, that carry information streams, such as digital data.

The term computer-readable medium is used herein to refer to any medium that participates in providing information to processor 1202, including instructions for execution. Such a medium may take many forms, including, but not limited to, non-volatile media, volatile media and transmission media. Non-volatile media include, for example, optical or magnetic disks, such as storage device 1208. Volatile media include, for example, dynamic memory 1204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1202, except for carrier waves and other signals.

Logic encoded in one or more tangible media includes one or both of processor instructions on a computer-readable storage media and special purpose hardware, such as ASIC 1220.

Network link 1278 typically provides information communication through one or more networks to other devices that use or process the information. For example, network link 1278 may provide a connection through local network 1280 to a host computer 1282 or to equipment 1284 operated by an Internet Service Provider (ISP). ISP equipment 1284 in turn provides data communication services through the public, world-wide packet-switching communication network of networks now commonly referred to as the Internet 1290. A computer called a server 1292 connected to the Internet provides a service in response to information received over the Internet. For example, server 1292 provides information representing video data for presentation at display 1214.

The invention is related to the use of computer system 1200 for implementing the techniques described herein. According to one embodiment of the invention, those techniques are performed by computer system 1200 in response to processor 1202 executing one or more sequences of one or more instructions contained in memory 1204. Such instructions, also called software and program code, may be read into memory 1204 from another computer-readable medium such as storage device 1208. Execution of the sequences of instructions contained in memory 1204 causes processor 1202 to perform the method steps described herein. In alternative embodiments, hardware, such as application specific integrated circuit 1220, may be used in place of or in combination with software to implement the invention. Thus, embodiments of the invention are not limited to any specific combination of hardware and software.

The signals transmitted over network link 1278 and other networks through communications interface 1270, carry information to and from computer system 1200. Computer system 1200 can send and receive information, including program code, through the networks 1280, 1290 among others, through network link 1278 and communications interface 1270. In an example using the Internet 1290, a server 1292 transmits program code for a particular application, requested by a message sent from computer 1200, through Internet 1290, ISP equipment 1284, local network 1280 and communications interface 1270. The received code may be executed by processor 1202 as it is received, or may be stored in storage device 1208 or other non-volatile storage for later execution, or both. In this manner, computer system 1200 may obtain application program code in the form of a signal on a carrier wave.

Various forms of computer readable media may be involved in carrying one or more sequence of instructions or data or both to processor 1202 for execution. For example, instructions and data may initially be carried on a magnetic disk of a remote computer such as host 1282. The remote computer loads the instructions and data into its dynamic memory and sends the instructions and data over a telephone line using a modem. A modem local to the computer system 1200 receives the instructions and data on a telephone line and uses an infra-red transmitter to convert the instructions and data to a signal on an infra-red a carrier wave serving as the network link 1278. An infrared detector serving as communications interface 1270 receives the instructions and data carried in the infrared signal and places information representing the instructions and data onto bus 1210. Bus 1210 carries the information to memory 1204 from which processor 1202 retrieves and executes the instructions using some of the data sent with the instructions. The instructions and data received in memory 1204 may optionally be stored on storage device 1208, either before or after execution by the processor 1202.

FIG. 13 illustrates a chip set 1300 upon which an embodiment of the invention may be implemented. Chip set 1300 is programmed to perform one or more steps of a method described herein and includes, for instance, the processor and memory components described with respect to FIG. 11 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1300, or a portion thereof, constitutes a means for performing one or more steps of a method described herein.

In one embodiment, the chip set 1300 includes a communication mechanism such as a bus 1301 for passing information among the components of the chip set 1300. A processor 1303 has connectivity to the bus 1301 to execute instructions and process information stored in, for example, a memory 1305. The processor 1303 may include one or more processing cores with each core configured to perform independently. A multi-core processor enables multiprocessing within a single physical package. Examples of a multi-core processor include two, four, eight, or greater numbers of processing cores. Alternatively or in addition, the processor 1303 may include one or more microprocessors configured in tandem via the bus 1301 to enable independent execution of instructions, pipelining, and multithreading. The processor 1303 may also be accompanied with one or more specialized components to perform certain processing functions and tasks such as one or more digital signal processors (DSP) 1307, or one or more application-specific integrated circuits (ASIC) 1309. A DSP 1307 typically is configured to process real-world signals (e.g., sound) in real time independently of the processor 1303. Similarly, an ASIC 1309 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1303 and accompanying components have connectivity to the memory 1305 via the bus 1301. The memory 1305 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1305 also stores the data associated with or generated by the execution of one or more steps of the methods described herein.

Alternatives and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

REFERENCES

The entire contents of each of the following are hereby incorporated by reference as if fully set forth herein, except as the terminology is inconsistent with the terminology presented herein.

Allmaier, G. N., C. Laschober, & W. W. Szymanski (2008). "Nano ES GEMMA and PDMA, New Tools for the Analysis of Nanobioparticles—Protein Complexes, Lipoparticles, and Viruses." *Journal of the American Society for Mass Spectrometry* 19: 1062-1068.

Aquila, A., M. S. Hunter, et al. (2012). "Time-resolved protein nanocrystallography using an X-ray free-electron laser." *Optics Express* 20(3): 2706-2716.

Barty, A., C. Caleman, et al. (2011). "Self-terminating X-ray diffraction gates femtosecond serial nanocrystallography measurements." *Nature Photonics* 6: 35-40.

Benner, W. H., et al. (2008). "Non-destructive characterization and alignment of aerodynamically focused particle beams using single particle charge detection." *Journal of Aerosol Science* 39: 917-928

Bogan, M. J., et al. (2008). "Single particle X-ray diffractive imaging." *Nano Letters* 8: 310-316.

Chapman, H., P. Fromme, et al. (2011). "Femtosecond x-ray protein nanocrystallography." *Nature* 470: 73-77.

DePonte, D. P., R. B. Doak, et al. (2009). "SEM imaging of liquid jets." *Micron,* 40(4): 507-509.

DePonte, D. P., K. Nass, et al. (2011). *Sample injection for pulsed x-ray sources*. Prague, Czech Republic, SPIE.

DePonte, D. P., U. Weierstall, et al. (2008). "Gas dynamic virtual nozzle for generation of microscopic droplet streams." *J. Phys. D: Appl. Phys.* 41: 195505.

Ganon-Calvo, A. M., D. P. DePonte, et al. (2010). "Liquid Capillary Micro/Nanojets in Free-Jet Expansion." *Small* 6(7): 822-824.

Hunter, M. S., D. P. DePonte, et al. (2011). "X-ray Diffraction from Membrane Protein Nanocrystals." *Biophysical Journal* 100(1): 198-206.

Johansson, L. C., D. Arnlund, et al. (2012). "Lipidic phase membrane protein femtosecond nanocrystallography." *Nature Methods* 9(3): 263-265.

Jung, J. H., J. E. Lee, & S. S. Kim (2009). "Generation of Nonagglomerated Airborne Bacteriophage Particles Using an Electrospray Technique." *Analytical Chemistry* 81: 2985-2990, doi:10.1021/ac802584z Koopmann, R., K. Cupelli, et al. (2012). "In vivo protein crystallization opens new routes in structural biology." *Nature Methods* 9(3): 259-262.

Ku, B. K., and S. S. Kim (2003). "Electrohydrodynamic spraying characteristics of glycerol solutions in vacuum." *Journal of Electrostatics* 57(2): 109-128.

Lomb, L., T. Barends, et al. (2011). "Radiation damage in protein serial femtosecond crystallography using an X-ray free-electron laser." *Physical Review B* 84: 214111.

Marginean, I., V. Znamenskiy, & A. Vertes (2006). "Charge Reduction in Electrosprays: Slender Nanojets as Intermediates." *Journal of Physical Chemistry B* 110: 6397-6404, doi:10.1021/jp055708k Modesto-Lopez, L. B., E. J. Thimsen, A. M. Collins, R. E. Blankenship & P. Biswas (2009). "Electrospray-assisted characterization and deposition of chlorosomes to fabricate a biomimetic light-harvesting device." *Energy & Environmental Science* 3: 216-222

Oshea, J. N., J. B. Taylor, et al. (2007). "Electrospray deposition of carbon nanotubes in vacuum." *Nanotechnology* 18(3): 035707.

Patriksson, A., E. Marklund, & D. van der Spoel (2007). "Protein structures under electrospray conditions." *Biochemistry* 46: 933-945.

Shapiro, D. A., H. N. Chapman, et al. (2008). "Powder diffraction from a continuous microjet of submicrometer protein crystals." *J. Synchrotron. Radiat.* 15(Pt 6): 593-599.

Sierra, R. G., H. Laksmono, et al. (2012). "Nanoflow electrospinning serial femtosecond crystallography." *Acta. Cryst. D.* 68(Pt 11): 1584-1587.

Smith, J. N., R. C. Flagan, & J. J. Beauchamp (2002). "Droplet evaporation and discharge dynamics in electrospray ionization." *Journal of Physical Chemistry A* 106: 9957-9967.

Swarbrick, J. C., J. B. Taylor, et al. (2006). "Electrospray deposition in vacuum." *Applied Surface Science* 252(15): 5622-5626.

Wortman, A., et al. (2007). "Shrinking Droplets in Electrospray Ionization and Their Influence on Chemical Equilibria." *Journal of the American Society for Mass Spectrometry* 18: 385-393.

What is claimed is:

1. A method comprising:
providing a sample liquid by flowing a plurality of a first target of interest with a carrier liquid; and
injecting the sample liquid through a capillary tube at a rate of about 4 microliters per minute or less than 4 microliters per minute, without a gas sheath flow, to form a cone or jet at a first position outside the capillary tube,
wherein
the first position is configured to intersect an X-ray beam;
the carrier liquid is electrically conductive; and
injecting the sample liquid further comprises injecting the sample liquid by applying a first voltage to the sample liquid upstream of the first position and a different second voltage to a counter electrode downstream of the first position.

2. A method as recited in claim 1, wherein injecting the sample liquid further comprises injecting the sample liquid at a rate of about 1 microliter per minute or less than 1 microliter per minute.

3. A method as recited in claim 1, wherein providing the sample liquid further comprises providing the sample liquid by flowing a plurality of nanoscale crystals of the first target of interest with the carrier fluid.

4. A method as recited in claim 3, wherein the nanoscale crystals are each about 500 nanometers or smaller than 500 nanometers in a largest dimension.

5. A method as recited in claim 1, wherein providing the sample liquid further comprises providing the sample liquid by flowing the carrier liquid in a concentric flow around the plurality of the first target of interest.

6. A method as recited in claim 1, wherein injecting the sample liquid further comprises injecting the sample liquid into a vacuum chamber through a capillary tube that terminates inside the vacuum chamber; the first position is inside the vacuum chamber; and the counter-electrode is disposed inside the vacuum chamber.

7. A method as recited in claim 6, wherein the viscosity of the carrier liquid is about 3 centipoise or greater than 3 centipoise.

8. A method as recited in claim 1, wherein the sample liquid in the jet has a diameter about equal to a diameter of the X-ray beam.

9. A method as recited in claim 8, wherein the sample liquid in the jet has a diameter of about one micrometer or less than one micrometer.

10. A method as recited in claim 6, wherein the vacuum chamber does not include a shroud to separate the vacuum chamber into two or more volumes pumped to different vacuum pressures.

11. A method as recited in claim 1, wherein injecting the sample liquid through the capillary tube further comprises injecting the sample liquid through a silicon capillary tube of diameter of about 25 micrometers, or about 95 micrometers or from 25 micrometers to 95 micrometers.

12. A method as recited in claim 1, wherein:
the X-ray beam is a femtosecond pulse high energy X-ray beam; and
the method further comprises measuring at an X-ray detector array an X-ray scattering pattern for the first target in the sample liquid in response to exposing the cone or jet of the sample liquid to the X-ray beam.

13. A method as recited in claim 1, wherein the carrier liquid comprises 10% by volume PEG 2000 and 30% sucrose solution with a sucrose concentration of about 1.1 Molar or about 1.4 Molar or in a range from 1.1 Molar to 1.4 Molar.

14. An apparatus comprising:
an inline mixing apparatus configured to produce a sample liquid from a plurality of a target of interest and an electrically conductive carrier fluid;
a capillary tube in fluid communication with the inline mixing apparatus at a first end configured to supply the sample liquid inside the capillary tube, wherein the capillary tube is open at a distal end opposite to the first end;
a voltage source configured to apply a first voltage to the sample liquid inside the capillary tube;
a counter electrode configured to be charged at a different second voltage; and
a source of an X-ray beam configured to intersect a cone or jet of the sample liquid at a first position between the distal end of the capillary tube and the counter electrode,
wherein
a different concentric tube configured to provide a gas sheath flow is omitted.

15. An apparatus comprising:
means for providing a sample liquid by flowing a plurality of a first target of interest with a carrier liquid; and
means for injecting the sample liquid through a capillary tube at a rate of about 4 microliter per minute or less than 4 microliters per minute without a gas sheath flow to form a cone or jet at a first position outside the capillary tube,
wherein
the first position is configured to intersect an X-ray beam;
the carrier liquid is electrically conductive; and
injecting the sample liquid further comprises injecting the sample liquid by applying a first voltage to the sample liquid upstream of the first position and a different second voltage to a counter electrode downstream of the first position.

16. A non-transitory computer-readable medium carrying one or more sequences of instructions, wherein execution of the one or more sequences of instructions by one or more processors causes an apparatus to perform:
applying a first voltage to a sample liquid and a different second voltage to a counter electrode;
injecting the sample liquid through a capillary tube at a rate of about 4 microliters per minute or less than 4 microliters per minute without a gas sheath flow, to form a cone or jet at a first position downstream of the capillary tube and upstream of the counter electrode; and
causing an X-ray source to generate an X-ray beam that intersects the cone or jet at the first position,
wherein the sample liquid comprises a plurality of a target of interest in flow with an electrically conductive carrier fluid.

17. An apparatus as recited in claim 14, wherein the inline mixing apparatus is a concentric flow apparatus configured to flow the carrier liquid in a concentric flow around the plurality of the first target of interest.

18. An apparatus as recited in claim 15, wherein the means for providing the sample liquid further comprises means for providing the sample liquid by flowing the carrier liquid in a concentric flow around the plurality of the first target of interest.

19. A non-transitory computer-readable medium as recited in claim 16, wherein injecting the sample liquid further comprises causing the carrier liquid to flow in a concentric flow around the plurality of the first target of interest.

* * * * *